(12) United States Patent
Locke et al.

(10) Patent No.: US 10,092,454 B2
(45) Date of Patent: Oct. 9, 2018

(54) WOUND-CONNECTION PADS FOR FLUID INSTILLATION AND NEGATIVE PRESSURE WOUND THERAPY, AND SYSTEMS AND METHODS

(71) Applicant: KCI Licensing, Inc., San Antonio, TX (US)

(72) Inventors: Christopher Brian Locke, Bournemouth (GB); Colin John Hall, Poole (GB); Aidan Marcus Tout, Alderbury (GB); Paul S. Slack, San Jose, CA (US); Thomas Paul Lawhorn, Denham Springs, LA (US); Timothy Mark Robinson, Basingstoke (GB)

(73) Assignee: KCI Licensing, Inc., San Antonio, TX (US)

( * ) Notice: Subject to any disclaimer, the term of this patent is extended or adjusted under 35 U.S.C. 154(b) by 852 days.

(21) Appl. No.: 14/498,653

(22) Filed: Sep. 26, 2014

(65) Prior Publication Data

US 2015/0018786 A1  Jan. 15, 2015

Related U.S. Application Data

(63) Continuation of application No. 13/009,220, filed on Jan. 19, 2011, now Pat. No. 8,870,837.
(Continued)

(51) Int. Cl.
*A61M 1/00* (2006.01)
*A61F 13/02* (2006.01)
(Continued)

(52) U.S. Cl.
CPC ...... *A61F 13/0216* (2013.01); *A61F 13/0226* (2013.01); *A61F 13/0253* (2013.01);
(Continued)

(58) Field of Classification Search
CPC .. A61B 90/05; A61F 13/0068; A61F 13/0216; A61F 13/0226; A61F 13/0253;
(Continued)

(56) References Cited

U.S. PATENT DOCUMENTS

| 1,355,846 A | 10/1920 | Rannells |
| 2,547,758 A | 4/1951 | Keeling |

(Continued)

FOREIGN PATENT DOCUMENTS

| AU | 550575 A1 | 3/1986 |
| AU | 745271 | 4/1999 |

(Continued)

OTHER PUBLICATIONS

N.A. Bagautdinov, "Variant of External Vacuum Aspiration in the Treatment of Purulent Diseases of the Soft Tissues," Current Problems in Modern Clinical Surgery: Interdepartmental Collection, edited by V. Ye Volkov et al. (Chuvashia State University, Cheboksary, U.S.S.R. 1986);pp. 94-96 (copy and certified translation).

(Continued)

*Primary Examiner* — Ariana Zimbouski

(57) ABSTRACT

Connection pads for coupling fluid-instillation and negative pressure wound therapy (NPWT) apparatuses to wound dressing, and methods and wound dressings for breaching a drape after coupling a wound dressing to a fluid-instillation and/or NPWT apparatus.

30 Claims, 9 Drawing Sheets

Related U.S. Application Data

(60) Provisional application No. 61/296,806, filed on Jan. 20, 2010.

(51) Int. Cl.
*B32B 37/06* (2006.01)
*B32B 37/10* (2006.01)
*B32B 37/12* (2006.01)
*B32B 38/00* (2006.01)

(52) U.S. Cl.
CPC ....... *A61F 13/0289* (2013.01); *A61M 1/0088* (2013.01); *B32B 37/06* (2013.01); *B32B 37/1045* (2013.01); *B32B 37/12* (2013.01); *B32B 38/0008* (2013.01); *A61M 1/0084* (2013.01); *A61M 2205/3344* (2013.01); *B32B 2310/028* (2013.01); *B32B 2310/0868* (2013.01); *B32B 2535/00* (2013.01)

(58) Field of Classification Search
CPC .. A61F 13/0289; A61M 1/0088; B32B 37/06; B32B 37/1045; B32B 37/12; B32B 38/0008
See application file for complete search history.

(56) References Cited

U.S. PATENT DOCUMENTS

| | | | |
|---|---|---|---|
| 2,632,443 A | 3/1953 | Lesher | |
| 2,682,873 A | 7/1954 | Evans et al. | |
| 2,910,763 A | 11/1959 | Lauterbach | |
| 2,969,057 A | 1/1961 | Simmons | |
| 3,066,672 A | 12/1962 | Crosby, Jr. et al. | |
| 3,367,332 A | 2/1968 | Groves | |
| 3,520,300 A | 7/1970 | Flower, Jr. | |
| 3,568,675 A | 3/1971 | Harvey | |
| 3,648,692 A | 3/1972 | Wheeler | |
| 3,682,180 A | 8/1972 | McFarlane | |
| 3,826,254 A | 7/1974 | Mellor | |
| 4,080,970 A | 3/1978 | Miller | |
| 4,096,853 A | 6/1978 | Weigand | |
| 4,139,004 A | 2/1979 | Gonzalez, Jr. | |
| 4,165,748 A | 8/1979 | Johnson | |
| 4,184,510 A | 1/1980 | Murry et al. | |
| 4,233,969 A | 11/1980 | Lock et al. | |
| 4,245,630 A | 1/1981 | Lloyd et al. | |
| 4,250,882 A | 2/1981 | Adair | |
| 4,256,109 A | 3/1981 | Nichols | |
| 4,261,363 A | 4/1981 | Russo | |
| 4,275,721 A | 6/1981 | Olson | |
| 4,284,079 A | 8/1981 | Adair | |
| 4,297,995 A | 11/1981 | Golub | |
| 4,333,468 A | 6/1982 | Geist | |
| 4,373,519 A | 2/1983 | Errede et al. | |
| 4,382,441 A | 5/1983 | Svedman | |
| 4,392,853 A | 7/1983 | Muto | |
| 4,392,858 A | 7/1983 | George et al. | |
| 4,419,097 A | 12/1983 | Rowland | |
| 4,465,485 A | 8/1984 | Kashmer et al. | |
| 4,475,909 A | 10/1984 | Eisenberg | |
| 4,480,638 A | 11/1984 | Schmid | |
| 4,525,166 A | 6/1985 | Leclerc | |
| 4,525,374 A | 6/1985 | Vaillancourt | |
| 4,540,412 A | 9/1985 | Van Overloop | |
| 4,543,100 A | 9/1985 | Brodsky | |
| 4,548,202 A | 10/1985 | Duncan | |
| 4,551,139 A | 11/1985 | Plaas et al. | |
| 4,569,348 A | 2/1986 | Hasslinger | |
| 4,605,399 A | 8/1986 | Weston et al. | |
| 4,608,041 A | 8/1986 | Nielsen | |
| 4,640,688 A | 2/1987 | Hauser | |
| 4,655,754 A | 4/1987 | Richmond et al. | |
| 4,664,662 A | 5/1987 | Webster | |
| 4,710,165 A | 12/1987 | McNeil et al. | |
| 4,733,659 A | 3/1988 | Edenbaum et al. | |
| 4,743,232 A | 5/1988 | Kruger | |
| 4,758,220 A | 7/1988 | Sundblom et al. | |
| 4,787,888 A | 11/1988 | Fox | |
| 4,826,494 A | 5/1989 | Richmond et al. | |
| 4,838,883 A | 6/1989 | Matsuura | |
| 4,840,187 A | 6/1989 | Brazier | |
| 4,863,449 A | 9/1989 | Therriault et al. | |
| 4,872,450 A | 10/1989 | Austad | |
| 4,878,901 A | 11/1989 | Sachse | |
| 4,897,081 A | 1/1990 | Poirier et al. | |
| 4,906,233 A | 3/1990 | Moriuchi et al. | |
| 4,906,240 A | 3/1990 | Reed et al. | |
| 4,919,654 A | 4/1990 | Kalt et al. | |
| 4,941,882 A | 7/1990 | Ward et al. | |
| 4,953,565 A | 9/1990 | Tachibana et al. | |
| 4,969,880 A | 11/1990 | Zamierowski | |
| 4,985,019 A | 1/1991 | Michelson | |
| 5,037,397 A | 8/1991 | Kalt et al. | |
| 5,086,170 A | 2/1992 | Luheshi et al. | |
| 5,092,858 A | 3/1992 | Benson et al. | |
| 5,100,396 A | 3/1992 | Zamierowski | |
| 5,134,994 A | 8/1992 | Say | |
| 5,149,331 A | 9/1992 | Ferdman et al. | |
| 5,167,613 A | 12/1992 | Karami et al. | |
| 5,176,663 A | 1/1993 | Svedman et al. | |
| 5,215,522 A | 6/1993 | Page et al. | |
| 5,232,453 A | 8/1993 | Plass et al. | |
| 5,261,893 A | 11/1993 | Zamierowski | |
| 5,278,100 A | 1/1994 | Doan et al. | |
| 5,279,550 A | 1/1994 | Habib et al. | |
| 5,298,015 A | 3/1994 | Komatsuzaki et al. | |
| 5,342,376 A | 8/1994 | Ruff | |
| 5,344,415 A | 9/1994 | DeBusk et al. | |
| 5,358,494 A | 10/1994 | Svedman | |
| 5,437,622 A | 8/1995 | Carion | |
| 5,437,651 A | 8/1995 | Todd et al. | |
| 5,527,293 A | 6/1996 | Zamierowski | |
| 5,549,584 A | 8/1996 | Gross | |
| 5,556,375 A | 9/1996 | Ewall | |
| 5,607,388 A | 3/1997 | Ewall | |
| 5,636,643 A | 6/1997 | Argenta et al. | |
| 5,645,081 A | 7/1997 | Argenta et al. | |
| 6,071,267 A | 6/2000 | Zamierowski | |
| 6,135,116 A | 10/2000 | Vogel et al. | |
| 6,241,747 B1 | 6/2001 | Ruff | |
| 6,287,316 B1 | 9/2001 | Agarwal et al. | |
| 6,290,685 B1* | 9/2001 | Insley | A61M 1/008 165/6 |
| 6,345,623 B1 | 2/2002 | Heaton et al. | |
| 6,458,109 B1 | 10/2002 | Henley et al. | |
| 6,488,643 B1 | 12/2002 | Tumey et al. | |
| 6,493,568 B1 | 12/2002 | Bell et al. | |
| 6,553,998 B2 | 4/2003 | Heaton et al. | |
| 6,814,079 B2 | 11/2004 | Heaton et al. | |
| 7,520,872 B2 | 4/2009 | Biggie et al. | |
| 7,651,484 B2* | 1/2010 | Heaton | A61M 1/0088 604/304 |
| 2002/0077661 A1 | 6/2002 | Saadat | |
| 2002/0115951 A1 | 8/2002 | Norstrem et al. | |
| 2002/0120185 A1 | 8/2002 | Johnson | |
| 2002/0143286 A1 | 10/2002 | Tumey | |
| 2003/0040687 A1 | 2/2003 | Boynton et al. | |
| 2004/0055387 A1 | 3/2004 | Miyazaki et al. | |
| 2005/0070835 A1* | 3/2005 | Joshi | A61M 1/0066 602/41 |
| 2006/0079852 A1 | 4/2006 | Bubb et al. | |
| 2007/0219512 A1 | 9/2007 | Heaton et al. | |
| 2008/0306456 A1* | 12/2008 | Riesinger | A61F 13/0203 604/316 |
| 2009/0005746 A1 | 1/2009 | Nielsen et al. | |
| 2009/0312727 A1 | 12/2009 | Heaton | |
| 2009/0326416 A1* | 12/2009 | McNulty | A61B 5/145 600/573 |

(56) References Cited

U.S. PATENT DOCUMENTS

FOREIGN PATENT DOCUMENTS

| | | |
|---|---|---|
| AU | 755496 | 2/2002 |
| CA | 2005436 | 6/1990 |
| DE | 26 40 413 A1 | 3/1978 |
| DE | 43 06 478 A1 | 9/1994 |
| DE | 295 04 378 U1 | 10/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 B1 | 8/2004 |
| GB | 692578 | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 B | 3/1999 |
| GB | 2 333 965 A | 8/1999 |
| JP | 4129536 | 4/1992 |
| JP | 2009295669 | 12/2009 |
| SG | 71559 | 3/1999 |
| WO | 80/02182 A1 | 10/1980 |
| WO | 87/04626 A1 | 8/1987 |
| WO | 90/10424 A1 | 9/1990 |
| WO | 93/09727 A1 | 5/1993 |
| WO | 94/20041 A1 | 9/1994 |
| WO | 96/05873 A1 | 2/1996 |
| WO | 97/18007 A1 | 5/1997 |
| WO | 99/13793 A1 | 3/1999 |
| WO | 0007653 A1 | 2/2000 |
| WO | 2007092397 A2 | 8/2007 |
| WO | 2008/100440 A1 | 8/2008 |
| WO | 2009071932 A2 | 6/2009 |

OTHER PUBLICATIONS

Louis C. Argenta, MD and Michael J. Morykwas, PhD; "Vacuum-Assisted Closure: A New Method for Wound Control and Treatment: Animal Studies & Basic Foundation"; Annals of Plastic Surgery, vol. 38, No. 6, Jun. 1997; pp. 553-562.
Susan Mendez-Eastmen, Rn; "When Wounds Won't Heal" RN Jan. 1998, vol. 61 (1); Medical Economics Company, Inc., Montvale, NJ, USA; pp. 20-24.
James H. Blackburn, II, MD, et al; "Negative-Pressure Dressings as a Bolster for Skin Grafts"; Annals of Plastic Surgery, vol. 40, No. 5, May 1998, pp. 453-457.
John Masters; "Reliable, Inexpensive and Simple Suction Dressings"; Letters to the Editor, British Journal of Plastic Surgery, 1998, vol. 51 (3), p. 267; Elsevier Science/The British Association of Plastic Surgeons, UK.
S.E. Greer, et al "The Use of Subatmospheric Pressure Dressing Therapy to Close Lymphocutaneous Fistulas of the Groin" British Journal of Plastic Surgery (2000), vol. 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, vol. 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; dated Nov. 23, 1995.
PCT International Search Report for PCT International Application PCT/GB98/02713; dated Jan. 8, 1999.
PCT Written Opinion; PCT International Application PCT/GB98/02713; dated Jun. 8, 1999.
PCT International Examination and Search Report, PCT International Application PCT/GB96/02802; dated Jan. 15, 1998 & dated Apr. 29, 1997.
PCT Written Opinion, PCT International Application PCT/GB96/02802; dated Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu. N., et al; "Active Wound Drainage", Vestnik Khirurgi, vol. 138, Issue 4, 1987, and 7 page English translation thereof.
Davydov, Yu. A., et al; "Bacteriological and Cytological Assessment of Vacuum Therapy for Purulent Wounds"; Vestnik Khirurgi, Oct. 1988, pp. 48-52, and 8 page English translation thereof.
Davydov, Yu. A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, p. 1.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., vol. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al.: "A Dressing System Providing Fluid Supply and Suction Drainage Used for Continuous or Intermittent Irrigation", Annals of Plastic Surgery, vol. 17, No. 2, Aug. 1986, pp. 125-133.
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovic, V. Ðukić, Ž. Maksimovie, Ð. Radak, and P. Peška, "Vacuum Therapy in the Treatment of Peripheral Blood Vessels," Timok Medical Journal 11 (1986), pp. 161-164 (copy and certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, "An Improved Sump Drain-Irrigation Device of Simple Construction," Archives of Surgery 105 (1972) pp. 511-513.
C.E. Tennant, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.A. Bagautdinov, "Vacuum and Vacuum-Sorption Treatment of Open Septic Wounds," in II All-Union Conference on Wounds and Wound Infections: Presentation Abstracts,

(56) References Cited

OTHER PUBLICATIONS edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

V.A.C.® Therapy Clinical Guidelines: A Reference Source for Clinicians (Jul. 2007).

Extended European Search Report corresponding to Application No. 117350744, dated Feb. 19, 2018.

Canadian Exam Report corresponding to Application No. 2784138, dated Jan. 26, 2017.

\* cited by examiner

WOUND-CONNECTION PADS FOR FLUID INSTILLATION AND NEGATIVE PRESSURE WOUND THERAPY, AND SYSTEMS AND METHODS

CROSS-REFERENCE TO RELATED APPLICATIONS

This application is a Continuation of U.S. patent application Ser. No. 13/009,220, filed Jan. 19, 2011 which claims priority to U.S. Provisional Patent Application No. 61/296,806, filed Jan. 20, 2010, which is incorporated herein in its entirety.

BACKGROUND

1. Field of the Invention

The present invention relates generally to healing of wounds and wound-treatment therapies. More particularly, but not by way of limitation, the present invention relates to systems and methods for improving the connection between a wound dressing and negative pressure wound therapy (NPWT) apparatuses and methods.

2. Background Information

Clinical studies and practice have shown that providing a reduced pressure in proximity to a tissue site augments and accelerates the growth of new tissue at the tissue site. The applications of this phenomenon are numerous, but application of reduced pressure has been particularly successful in treating wounds. This treatment (frequently referred to in the medical community as "negative pressure wound therapy," "reduced pressure therapy," or "vacuum therapy") provides a number of benefits, including faster healing and increased formulation of granulation tissue. Typically, reduced pressure is applied to tissue through a wound insert (e.g., a porous pad or other manifold device). The wound insert typically contains cells or pores that are capable of distributing reduced pressure to the tissue and channeling fluids that are drawn from the tissue. The wound insert can be incorporated into a wound dressing having other components that facilitate treatment, such as, for example, a drape (e.g., adhesive surgical drape). Instillation of fluids (e.g., irrigation fluids and/or medicaments) may be used in conjunction with negative pressure wound therapy to promote healing and/or improve efficacy.

While NPWT has been highly successful in the promotion of wound closure, healing many wounds previously thought largely untreatable, some difficulty remains. One common component of an NPWT system is a device or structure (e.g., connection pad) that connects the vacuum (or negative pressure) source (e.g., a vacuum pump) and/or the fluid source to a wound dressing or components (e.g., foam wound insert within the wound dressing).

It may be difficult to accurately characterize the pressure level at the tissue site by simply measuring the level of reduced pressure that the reduced pressure source is providing, either at the source or in the conduit lines connecting the source to the wound dressing. Fluid flow within the primary lumen of tubing associated with NPWT systems may prevent pressure level measurements at the apparatus (e.g., vacuum source) from accurately indicating the level or stability of the pressure at the wound itself.

While NPWT has been used for some time, NPWT wound dressings, and their connection to NPWT apparatuses can be difficult to use and time consuming to apply (e.g., due at least in part to the number of connections which must be made between wound dressings and connection pads, and between connection pads and conduits to the NPWT apparatus).

SUMMARY

The present disclosure includes embodiments of wound dressings and connection pads.

Some embodiments of the present vacuum and/or fluid-delivery connection pads comprise: a body having a dressing side and a connection side, the dressing side including a cavity having an upper portion and a base portion, and a flange surrounding the base portion of the cavity, and the connection side including: a multi-lumen vacuum and pressure-sensor connection configured to be coupled to a vacuum source and a pressure sensor, and having a vacuum lumen terminating at an upper portion of the cavity, and a first pressure-sensor lumen extending to the base-portion of the cavity, a lateral portion of the first pressure-sensor lumen being open to the cavity.

In some embodiments, the body defines at least one second pressure-sensor lumen extending to the base-portion of the cavity and in fluid communication with the first pressure-sensor lumen, a lateral portion of the second pressure-sensor lumen being open to the cavity. In some embodiments, the multi-lumen vacuum and pressure-sensor connection comprises an annular pressure-sensor lumen disposed around the vacuum lumen, the annular pressure-sensor lumen in communication with the first and/or second pressure-sensor lumen(s).

Some embodiments further comprise a single-lumen fluid-delivery connection configured to be coupled to a fluid source and having a fluid-delivery lumen extending into the cavity. In some embodiments, the fluid-delivery lumen extends to a fluid-delivery ring disposed around at least a portion of the cavity and configured to permit fluid to be delivered around the cavity. In some embodiments, at least a portion of the surface defining the cavity includes a plurality of grooves extending from the upper portion of the cavity to the base portion of the cavity.

In some embodiments, a lower edge of the flange comprises a plurality of radial guide channels extending radially outward from the base portion of the cavity and terminating within the flange. In some embodiments, the radial guide channels are each serrated perpendicular to the radial direction. In some embodiments, the lower edge of the flange comprises a plurality of arcuate collection channels concentric with the cavity, each arcuate collection channel extending around a portion of the cavity. In some embodiments, the arcuate collection channels include a plurality of arcuate perimeter collection channels and a plurality of arcuate intermediate collection channels that are disposed between the arcuate perimeter collection channels and the cavity. In some embodiments, the plurality of radial guide channels extend outward from the base portion of the cavity and each terminate at one of the arcuate perimeter collection channels. In some embodiments, each of the radial guide channels is serrated perpendicular to the radial direction and comprises serrations with different depths. In some embodiments, each radial guide channel comprises a central serration having a depth and a plurality of peripheral serrations adjacent the central serration, each peripheral serration having a depth that is less than the depth of the central serration.

In some embodiments, at least a portion of the surface defining the cavity defines a shelf substantially parallel to the flange adjacent the base portion of the cavity. In some embodiments, the pressure-sensor lumen(s) are not in fluid communication with the fluid-delivery lumen through the body.

Some embodiments of the present vacuum and fluid-delivery connection pads comprise: a body having a dressing side and a connection side, the dressing side including a cavity having an upper portion and a base portion, and a flange surrounding the base portion of the cavity, and the connection side including: a single-lumen fluid-delivery connection configured to be coupled to a fluid source and having a fluid-delivery lumen extending into the cavity, and a multi-lumen vacuum and pressure-sensor connection configured to be coupled to a vacuum source and a pressure sensor, and having a vacuum lumen terminating at an upper portion of the cavity, and a first pressure-sensor lumen extending into the cavity, a lateral portion of the first pressure-sensor lumen open to the cavity. In some embodiments, the body defines at least one second pressure-sensor lumen extending into the cavity and in fluid communication with the first pressure-sensor lumen, a lateral portion of the second pressure-sensor lumen open to the cavity. In some embodiments, the multi-lumen vacuum and pressure-sensor connection comprises an annular pressure-sensor lumen disposed around the vacuum lumen, the annular pressure-sensor lumen in communication with the first and second pressure-sensor lumens.

Some embodiments further comprise: a ring of adhesive coupled to the flange. In some embodiments, the adhesive comprises a hydrogel. In some embodiments, the adhesive comprises a pressure-sensitive adhesive. In some embodiments, the flange comprises a lower side configured to face a wound dressing if the pad is coupled to a wound dressing, and where the adhesive is coupled to the lower side of the flange. In some embodiments, the flange is configured to be coupled to a drape by at least one of: radio-frequency (RF) welding, ultrasonic welding, or adhesive. In some embodiments, the flange is coupled to a drape of a wound dressing. In some embodiments, the flange is coupled to the drape by at least one of: radio-frequency (RF) welding, ultrasonic welding, or adhesive.

Some embodiments of the present vacuum connection pads comprise: a body having a dressing side and a connection side, the dressing side including a cavity having an upper portion and a base portion, and a flange surrounding the base portion of the cavity, and the connection side including: a single-lumen vacuum connection configured to be coupled to a vacuum source and having a vacuum lumen in communication with the cavity, a pressure-sensor connection configured to be coupled to a pressure sensor, and having a first pressure-sensor lumen extending into the cavity, a lateral portion of the first pressure-sensor lumen open to the cavity. In some embodiments, the body defines at least one second pressure-sensor lumen extending into the cavity and in fluid communication with the first pressure-sensor lumen, a lateral portion of the second pressure-sensor lumen open to the cavity. In some embodiments, the body has a multi-lumen connection including the vacuum connection and the pressure-sensor connection, and where the pressure-sensor connection comprises an annular pressure-sensor lumen disposed around the vacuum lumen, the annular pressure-sensor lumen in communication with the first and second pressure-sensor lumens.

Some embodiments of the present fluid-delivery connection pads comprise: a body having a dressing side and a connection side, the dressing side including a surface defining a cavity having an upper portion and a base portion, and a flange surrounding the base portion of the cavity, the connection side including a fluid-delivery connection having a fluid-delivery lumen in fluid communication with an upper portion of the cavity and configured to be coupled to a fluid source. In some embodiments, the surface defining the cavity includes a plurality of grooves extending from the upper portion of the cavity to the base portion of the cavity. In some embodiments, the grooves intersect a lower peripheral edge of the base portion such that the lower peripheral edge has a saw-toothed configuration. In some embodiments, the flange has a substantially smooth and substantially planar lower surface. In some embodiments, a lower edge of the flange comprises a plurality of radial guide channels extending radially outward from the base portion of the cavity and terminating within the outer perimeter of the flange. In some embodiments, the radial guide channels are each serrated. In some embodiments, the lower edge of the flange comprises a plurality of arcuate collection channels concentric with the cavity, each arcuate collection channel extending around a portion of the cavity. In some embodiments, the arcuate collection channels include a plurality of arcuate perimeter collection channels and a plurality of arcuate intermediate collection channels that are disposed between the arcuate perimeter collection channels and the cavity. In some embodiments, the plurality of radial guide channels extend outward from the base portion of the cavity and each terminate at one of the arcuate perimeter collection channels. In some embodiments, the plurality of radial grooves are spaced around the flange at equiangular intervals. In some embodiments, each of the radial guide channels is serrated and comprises serrations with different depths. In some embodiments, each radial guide channel comprises a central serration having a depth and a plurality of peripheral serrations adjacent the central serration, each peripheral serration having a depth that is less than the depth of the central serration. In some embodiments, the fluid-delivery lumen extends laterally into the cavity between the upper portion and base. In some embodiments, the fluid-delivery lumen has an open end facing a side of the cavity. In some embodiments, a lateral portion of the fluid-delivery lumen opens downward toward the base portion of the cavity. In some embodiments, the end of the fluid-delivery lumen is closed such that the fluid-delivery lumen is only in fluid communication with the cavity through the downward opening from the fluid-delivery lumen.

Some embodiments further comprise: a ring of adhesive coupled to the flange. In some embodiments, the adhesive comprises a hydrogel. In some embodiments, the adhesive comprises a pressure-sensitive adhesive. In some embodiments, the flange comprises a lower side configured to face a wound dressing if the pad is coupled to a wound dressing, and where the adhesive is coupled to the lower side of the flange. In some embodiments, the flange is configured to be coupled to a drape by at least one of: radio-frequency (RF) welding, ultrasonic welding, or adhesive. In some embodiments, the flange is coupled to a drape of a wound dressing. In some embodiments, the flange is coupled to the drape by at least one of radio-frequency (RF) welding, ultrasonic welding, or adhesive.

Some embodiments of the present fluid-delivery connection pads comprise: a body having a dressing side and a connection side, the dressing side including a cavity having an upper portion and a base portion, a flange surrounding the base portion of the cavity, and a fluid-delivery ring disposed around at least a portion of the cavity and configured to permit fluid to be delivered around the cavity, and the connection side including: a single-lumen fluid-delivery connection configured to be coupled to a fluid source and having a fluid-delivery lumen in communication with the fluid-delivery ring, and a pressure-sensor connection configured to be coupled to a vacuum source and a pressure sensor, and having a first pressure-sensor lumen extending into the cavity, a lateral portion of the first pressure-sensor lumen open to the cavity.

In some embodiments, the body defines at least one second pressure-sensor lumen having a lower end extending into the cavity and in fluid communication with the first pressure-sensor lumen, a lateral portion of the second pressure-sensor lumen open to the cavity. In some embodiments, the body has a multi-lumen connection including the fluid-delivery connection and the pressure-sensor connection, and where the pressure-sensor connection comprises an annular pressure-sensor lumen disposed around the fluid-delivery lumen, the annular pressure-sensor lumen in communication with the first and second pressure-sensor lumens.

Some embodiments of the present fluid-delivery connection pads comprise: a body having a dressing side and a connection side, the dressing side including a surface defining a cavity having an upper portion and a base portion, and a flange surrounding the base portion of the cavity, the connection side including: a fluid-delivery connection having a fluid-delivery lumen in fluid communication with an upper portion of the cavity and configured to be coupled to a fluid source, and a first pressure-sensor lumen extending into the cavity and configured to be coupled to a pressure sensor, a lateral portion of the first pressure-sensor lumen open to the cavity; where the surface defining the cavity includes an open channel at the upper portion of the cavity, the open channel coupled to the fluid-delivery lumen. In some embodiments, the body defines at least one second pressure-sensor lumen extending into the cavity and in fluid communication with the first pressure-sensor lumen, a lateral portion of the second pressure-sensor lumen open to the cavity. In some embodiments, the body has a multi-lumen connection including the fluid-delivery connection and the pressure-sensor connection, and where the pressure-sensor connection comprises an annular pressure-sensor lumen disposed around the fluid-delivery lumen, the annular pressure-sensor lumen in communication with the first and second pressure-sensor lumens. In some embodiments, a first portion of the surface on a first side of the open channel includes a plurality of plurality of grooves extending from the open channel to the base portion of the cavity. In some embodiments, a second portion of the surface on a second side of the open channel defines a shelf substantially parallel to the flange adjacent the base portion of the cavity. In some embodiments, the pressure-sensor lumens are not in fluid communication with the fluid-delivery lumen through the body. In some embodiments, the body defines a lower end of each of the first and second pressure-sensor lumens substantially even with the shelf, and where the body further defines one or more notches at the lower end of each of the first and second pressure-sensor lumens extending between a lateral portion of the pressure-sensor lumen and the cavity. In some embodiments, the first and second pressure-sensor lumens extend into the cavity at an angle substantially perpendicular to the open channel.

Some embodiments further comprise: a ring of adhesive coupled to the flange. In some embodiments, the adhesive comprises a hydrogel. In some embodiments, the adhesive comprises a pressure-sensitive adhesive. In some embodiments, the flange comprises a lower side configured to face a wound dressing if the pad is coupled to a wound dressing, and where the adhesive is coupled to the lower, side of the flange. In some embodiments, the flange is configured to be coupled to a drape by at least one of: radio-frequency (RF) welding, ultrasonic welding, or adhesive. In some embodiments, the flange is coupled to a drape of a wound dressing. In some embodiments, the flange is coupled to the drape by at least one of: radio-frequency (RF) welding, ultrasonic welding, or adhesive.

Some embodiments of the present methods of coupling a wound dressing to a patient, comprise: disposing a wound insert adjacent to a wound of a patient; coupling a drape to skin of the patient adjacent the wound such that the drape covers the wound insert and the wound, and defines a space between the wound and the drape; coupling a connection pad to the drape, the connection pad configured to be coupled to a fluid source such that the fluid source can be activated to deliver fluid to the connection pad; and breaching the drape, after coupling the connection pad to the drape, to enable fluid communication between the space and the connection pad. In some embodiments, breaching the drape comprises delivering through the fluid delivery pad a solvent to the drape, the solvent configured to dissolve a portion of the drape to permit fluid communication between the space and the connection pad. Some embodiments further comprise: disposing a container of a first solvent between the fluid delivery connection pad and the drape, the first solvent configured to dissolve a portion of the drape, the container configured to dissolve in the presence of a second solvent. In some embodiments, breaching the drape comprises delivering the second solvent to the container through the connection pad such that the container dissolves to release the first solvent, and the first solvent dissolves a portion of the drape.

Any embodiment of any of the present systems and/or methods can consist of or consist essentially of—rather than comprise/include/contain/have—any of the described steps, elements, and/or features. Thus, in any of the claims, the term "consisting of" or "consisting essentially of" can be substituted for any of the open-ended linking verbs recited above, in order to change the scope of a given claim from what it would otherwise be using the open-ended linking verb.

Details associated with the embodiments described above and others are presented below.

BRIEF DESCRIPTION OF THE DRAWINGS

The following drawings illustrate by way of example and not limitation. For the sake of brevity and clarity, every feature of a given structure is not always labeled in every figure in which that structure appears. Identical reference numbers do not necessarily indicate an identical structure. Rather, the same reference number may be used to indicate a similar feature or a feature with similar functionality, as may non-identical reference numbers.

DESCRIPTION OF ILLUSTRATIVE EMBODIMENTS

The term "coupled" is defined as connected, although not necessarily directly, and not necessarily mechanically; two items that are "coupled" may be integral with each other. The terms "a" and "an" are defined as one or more unless this disclosure explicitly requires otherwise. The terms "substantially," "approximately," and "about" are defined as largely but not necessarily wholly what is specified, as understood by a person of ordinary skill in the art.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a method that "comprises," "has," "includes" or "contains" one or more steps possesses those one or more steps, but is not limited to possessing only those one or more steps. Likewise, a connection pad that "comprises," "has," "includes" or "contains" one or more elements possesses those one or more elements, but is not limited to possessing only those elements. For example, in a connection pad that comprises a fluid-delivery connection and a pressure-sensor connection, the connection pad includes the specified elements but is not limited to having only those elements. For example, such a connection pad could also include a vacuum connection.

Further, a device or structure that is configured in a certain way is configured in at least that way, but it can also be configured in other ways than those specifically described.

Figure 1:
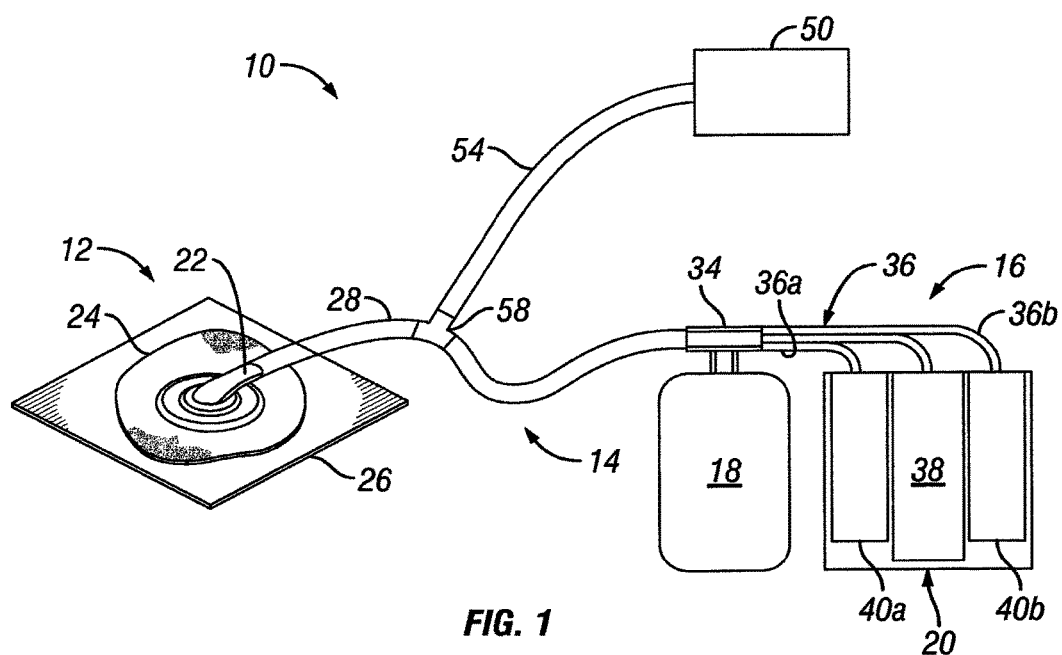
FIG. 1 depicts a partially schematic, perspective view of the general arrangements of the components of a negative pressure wound treatment (NPWT) system including one embodiment of the present connection pads.

Referring now to the drawings, and more particularly to FIG. 1, one example of a negative pressure wound treatment (NPWT) system 10 is shown that can incorporate and/or comprise embodiments of the present connection pads. In the embodiment shown, system 10 comprises wound dressing 12, conduit 14, and vacuum apparatus 16 coupled to conduit 14 and thereby to wound dressing 12. In the embodiment shown, wound dressing 12 comprises a foam wound insert 24 (e.g., distribution manifold 24), and a drape 26. Drape 26 is configured to be coupled to skin of a patient adjacent the wound such that drape 26 covers wound insert 24 and the wound, and forms a space between a wound surface of the wound and drape 26. Wound insert 24 can comprise any suitable foam, such as, for example, an open-celled foam (which may also be reticulated), and/or the like. Wound dressing 12 can comprise and/or can be coupled to conduit 14 by a connection pad 22, as shown. Connection pad 22 is typically coupled to drape 26 by an adhesive or the like. For example, in some embodiments, drape 26 has a hole or aperture through its center such that drape 26 fits around connection pad 22 (e.g., around a flange of connection pad 22), such that a lower adhesive side of drape 26 can adhere to connection pad 22 and the skin of the patient adjacent to the wound. In other embodiments, drape 26 is provided with a hole in its center (e.g., before or after drape 26 is coupled to the skin of the patient to cover the wound and wound insert 24), and a secondary drape is coupled over a portion of connection pad 22 (e.g., a flange of connection pad 22) to couple the connection pad to drape 26.

In the embodiment shown, conduit 14 comprises a multi-lumen tube including one or more tubing sections 28 which, as an assembled structure, provide a continuous conduit between connection pad 22 and a container connector 34 positioned on a fluid container 18. As generally known in the art, liquid and other exudates drawn by NPWT system 10 are removed from conduit 14 at container connector 34, and deposited in and retained within container 18. In the embodiment shown, instrumentation tubes 36a and 36b extend from container connector 34 to instrumentation components 20. In the embodiment shown, instrumentation components 20 comprise a vacuum source 38 and pressure monitoring instrument components 40a and 40b (e.g., pressure sensors for measuring pressure), which are described in more detail in U.S. patent application Ser. No. 11/722,802. Each of the instrument components 20 is individually associated with one of three isolated conduits (tubes or lumens) that extend from reduced pressure adapter 22 into vacuum apparatus 16.

In the embodiment shown, system 10 further comprises a fluid source 50 coupled to wound dressing 12 by a conduit 54 and a tee-fitting 58. In the embodiment shown, vacuum apparatus 16 and fluid source 50 are shown separately; however, in some embodiments, fluid source 50 and vacuum apparatus 16 may be commonly housed. In some embodiments, fitting 58 can provide communication between a multi-lumen conduit 54 and multi-lumen conduit 28. However, in other embodiments, fitting 58 is configured to enable fluid communication between the primary lumen of conduit 28 and a single lumen of conduit 54, while permitting communication between the peripheral lumens of conduit 28 on both sides of fitting 58. In some embodiments, fitting 58 comprises a switch valve or the like such that communication can be selectively permitted between wound dressing 12 and fluid source 50, and between wound dressing 12 and vacuum apparatus 16. In other embodiments, fluid source 50 is separately coupled to wound insert 12, such as, for example, by way of a separate lumen in connection pad 22, or by way of a separate connection pad 22. In the embodiments in which fluid source 50 is separately coupled to wound insert 12, tee fitting 58 may be omitted.

In various embodiments of wound insert 12 (e.g., where wound insert 12 is large or elongated such as for a large wound), multiple connection pads 22 may be used or employed with (e.g., coupled to) a single wound dressing 12. For example, in some such embodiments, a first connection pad 22 can be coupled to fluid source 50, and a second connection pad 22 can be coupled to vacuum apparatus 16, such that fluid can introduced to the wound insert through the first connection pad, and vacuum or negative pressure (relative to atmospheric pressure) can be applied to the wound insert via the connection pad that is coupled to vacuum apparatus 16 (e.g., such that fluid can travel through a larger portion of wound insert 24 and/or to contact a greater portion of the wound before being extracted through the second connection pad).

Figure 2:
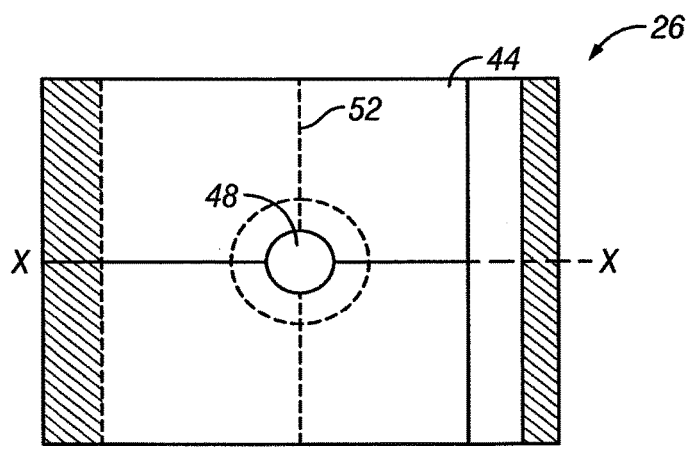
FIG. 2 depicts a top view of a drape for use with the present wound dressings and connection pads.

Referring now to FIG. 2, an example of a drape 26 is shown. In the embodiment shown, drape 26 comprises a film 44 (e.g., a polyurethane film) coated one side with a pressure sensitive adhesive (e.g., a pressure-sensitive acrylic resin adhesives), and having a hole 48 extending through film 44. Hole 48 is typically sized to correspond to one or more corresponding openings in a lower side of connection pad 22 and may be cut or otherwise formed after a drape is coupled to (e.g., adhered to) a patient. Drape 26 (e.g., film 44) can be sized such that drape 26 is sufficiently large to extend beyond the borders of a wound to which wound dressing 12 is applied and such that the adhesive of drape 26 contacts and adheres to a sufficient portion of the patient's skin adjacent to the wound to provide a substantially sealed environment between drape 26 and the wound. In other embodiments, drape 26 can comprise two parts or pieces. For example, drape 26 of FIG. 2 can be cut or have a border along line 52 and the two pieces can be sealed with surgical tape and/or the like placed over line 52.

Figure 3:
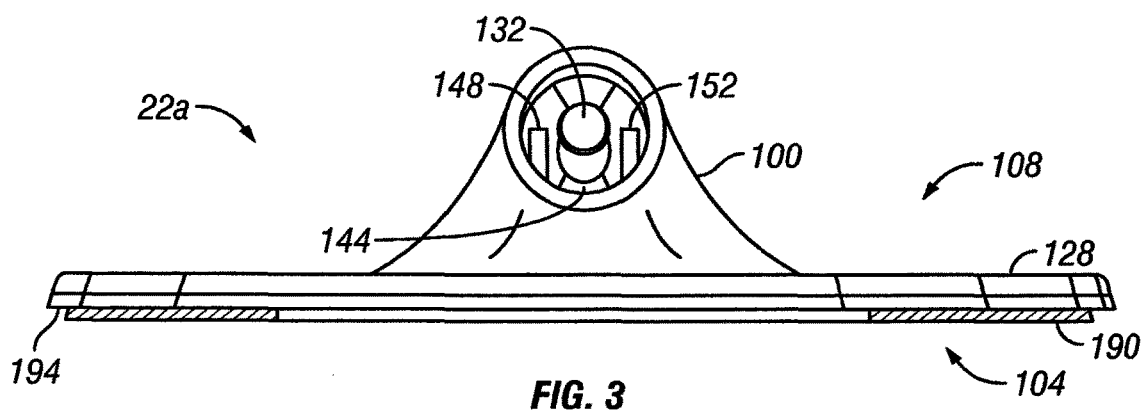
FIG. 3 depicts a side view of one embodiment of the present connection pads.
Figure 4:
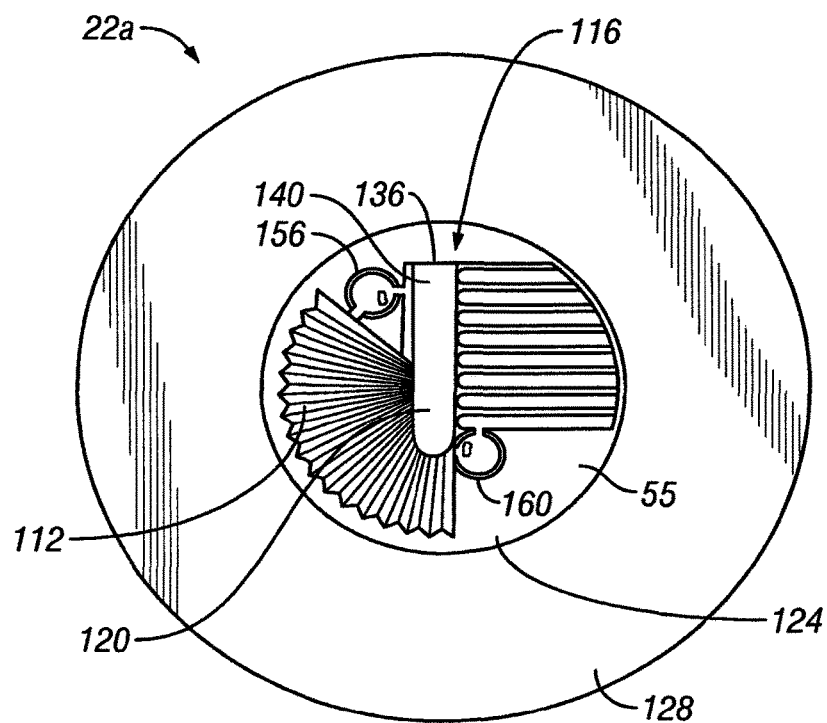
FIG. 4 depicts a bottom view of the connection pad of FIG. 3.
Figure 5:
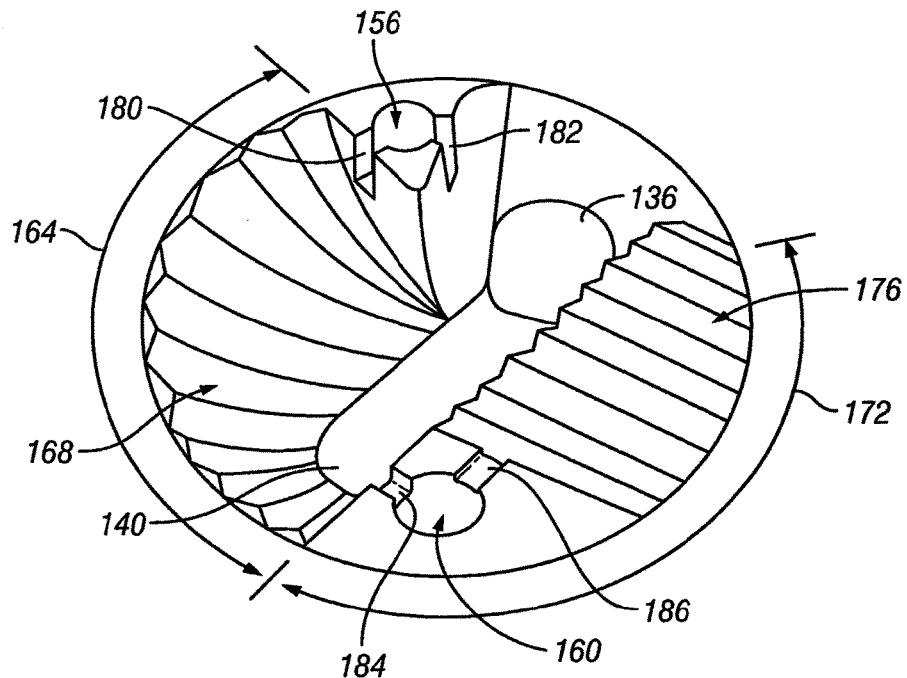
FIG. 5 depicts a bottom perspective view of a portion of the connection pad of FIG. 4.

Referring now to FIGS. 3-5, enlarged views are shown of first embodiment 22a of the present connection pads. In the embodiment shown, connection pad 22a comprises a body 100 having a dressing side 104 and a connection side 108. Dressing side 104 includes a surface 112 defining a cavity 116 (e.g., a domed cavity) having an upper portion 120 and a base portion 124. In the embodiment shown, connection pad 22a also includes a flange 128 (e.g., a substantially planar flange) surrounding base portion 124 of cavity 116. In the embodiment shown, connection side 108 includes a lumen 132 (e.g., a fluid-delivery and/or vacuum lumen 132) in fluid communication with an upper portion 120 of cavity 116, and configured to be coupled to a fluid source (e.g., fluid source 50, such as, for example, by way of conduit 54) and/or a vacuum source. More particularly, lumen 132 is in fluid communication with upper portion 120 of cavity 116 by way of primary port 136 and open channel 140 disclosed adjacent top portion 120 of cavity 116, as shown. In the embodiment shown, connection side 108 further includes an annular pressure-sensor lumen 144 in communication with cavity 116 and configured to be coupled to the one or more pressure sensors of vacuum apparatus 16 (e.g., tubes 36 and pressure monitoring instrument components 40a and 40b). Particularly, in the embodiment shown, annular pressure-sensor lumen 144 is in communication with cavity 116 by way of ancillary lumen interfaces 148, 152 which are in communication with pressure-sensor lumens 156 and 160, respectively, and thereby in communication with cavity 116. In other embodiments, body 100 may not include annular pressure-sensor lumen 144 (e.g., first pressure-sensor lumen 156 can extend to the connection side to be coupled to a pressure sensor). Further, in other embodiments, second pressure-sensor lumen 160 may be omitted. In the embodiment shown, annular pressure-sensor lumen 144 is disposed around lumen 132 (e.g., such that annular pressure-sensor lumen 144 is concentric with lumen 132). In the embodiment shown, surface 112 defining cavity 116 includes open channel 140 extending into upper portion 120 of cavity 116, and open channel 140 is coupled to and in communication with lumen 132 via port 136. More particularly, in the embodiment shown, open channel 140 is disposed at the apex of cavity 116.

In the embodiment shown, a first portion 164 of surface 112 on a first side of open channel 140, as shown, includes a plurality of grooves 168 extending from open channel 140 to base portion 124 of cavity 116. Grooves 168 are configured to direct fluid from and/or to open channel 140, port 136, and fluid lumen 132. In the embodiment shown, a second portion 172 on a second side of open channel 140 defines a shelf 172 that is substantially parallel to (and/or co-planar with) planar flange 128. As shown, shelf 172 also comprises a plurality of serrations or grooves 176. Grooves 176 are also configured to direct fluid to or from open channel 140, and/or away from lumens 156 and 160, such that as fluid is delivered and/or removed from cavity 116 and/or wound dressing 12, fluid is generally directed past lumens 156 and 160 such that lumens 156 and 160 remain substantially unobstructed to permit vacuum apparatus 16 to sense the pressure or negative pressure within cavity 116 and/or wound dressing 12.

In the embodiment shown, fluid lumen 132 is not in fluid communication with lumens 156, 160 through body 100. In particular, although lumens 156, 160 may be permitted to communicate fluidly with lumen 132 (e.g., port 136) within and through cavity 116, within the solid portion of body 100 lumens 156, 160 are separate and distinct from fluid lumen 132 and port 136. In this way, vacuum apparatus 16 is permitted to sense pressure or negative pressure within open cavity 116 and/or wound dressing 12 separately from (e.g., not entirely dependent on) fluid and/or negative pressure in lumen 132. Additionally, in the embodiment shown, a lateral portion of each pressure-sensor lumen 156, 160 is open into cavity 116. More particularly, in the embodiment shown, body 100 defines notches 180 and 182 extending from a lateral portion of lumen 156 into cavity 116, and body 100 defines notches 184 and 186 extending from a lateral portion of lumen 160 into cavity 116. Notches 180, 182, 184, and 186 are configured to improve communication between lumens 156, 160 and cavity 116, so as to improve the ability of vacuum apparatus 16 to sense and/or monitor pressure or negative pressure at the wound (e.g., in cavity 116 and/or in wound dressing 12), especially, for example, where opening 48 in drape 26 is small, roughly cut, not fully made, off center, and/or is otherwise not optimally formed such that drape 26 would otherwise interfere and/or partially block the lumens 156, 160.

In the embodiment shown, body 100 also defines a lower end of each pressure-sensor lumen 156 and 160 that is substantially even with shelf 172. In the embodiment shown, at the lower end of each lumen 156 and 160, each lumen 156 and 160 extends into cavity 116 at an angle that is substantially perpendicular to open channel 140 (e.g., a longitudinal axis of open channel 140. In some embodiments, the lower end of each pressure-sensor lumen 156, 160 is offset from flange 128 (e.g., stops a distance short of the lower surface of the flange 128), such as, for example, by a distance of equal to, greater than, less than, or between any of, 0.1, 0.2, 0.3, 0.4, 0.5, 0.6, 0.7, 0.8, 0.9, 1 mm). In the embodiments where the lower end of each lumen 156, 160 is even with the lower surface of flange 128, body 100 is configured such that the lower end of each lumen 156, 160 is adjacent to and/or abuts wound insert 24 when connection pad 22a is coupled to wound dressing 12 (e.g., wound insert 24). In this way, body 100 is configured such that fluid being delivered to and/or drawn into cavity 116 is largely directed past lumens 156, 160 such that the fluid does not interfere with the pressure sensing functionality of the lumens 156 and 160, and notches 180, 182, 184, 186 still permit lumens 156, 160 to communicate with cavity 116 and/or wound dressing 12 to sense pressure or negative pressure within cavity 116 and/or wound dressing 12.

Additionally, as shown in FIG. 3 but omitted from FIGS. 4 and 5, some embodiments of connection pads 22a further comprise a ring of adhesive 190 (shown in partial cross-section) coupled to flange 128 of body 100. In particular, in the embodiment shown, flange portion 128 of body 100 comprises a lower side 194 configured to face wound dressing 12 if connection pad 22a is coupled to wound dressing 12. Adhesive ring 190 can comprise any suitable adhesive, such as, for example, an adhesive comprising hydrogel, hydrocolloids, a pressure-sensitive adhesive, and/or any other suitable adhesive. In this embodiment, adhesive ring 190 is configured such that if connection pad 22a is coupled to wound dressing 12 can adhere to wound insert 24. In other embodiments, adhesive ring 190 (or a second adhesive ring) can be coupled to an upper side of flange portion 128 (e.g., a side opposite lower side 194) to adhere to a drape 26 placed over the wound insert 24. In some embodiments, the adhesive can be removable and/or re-appliable such that even after initially adhering to a portion of dressing, the position of connection pad 22a relative to wound dressing 12 can be adjusted as needed or desired. In other embodiments, connection pad 22a can be permanently coupled (e.g., during manufacture) to drape 26 prior to receipt by a user (e.g., doctor, nurse, etc.) by any suitable means, such as, for example, radio-frequency (RF) welding, ultrasonic welding, and/or the like.

Figure 6:
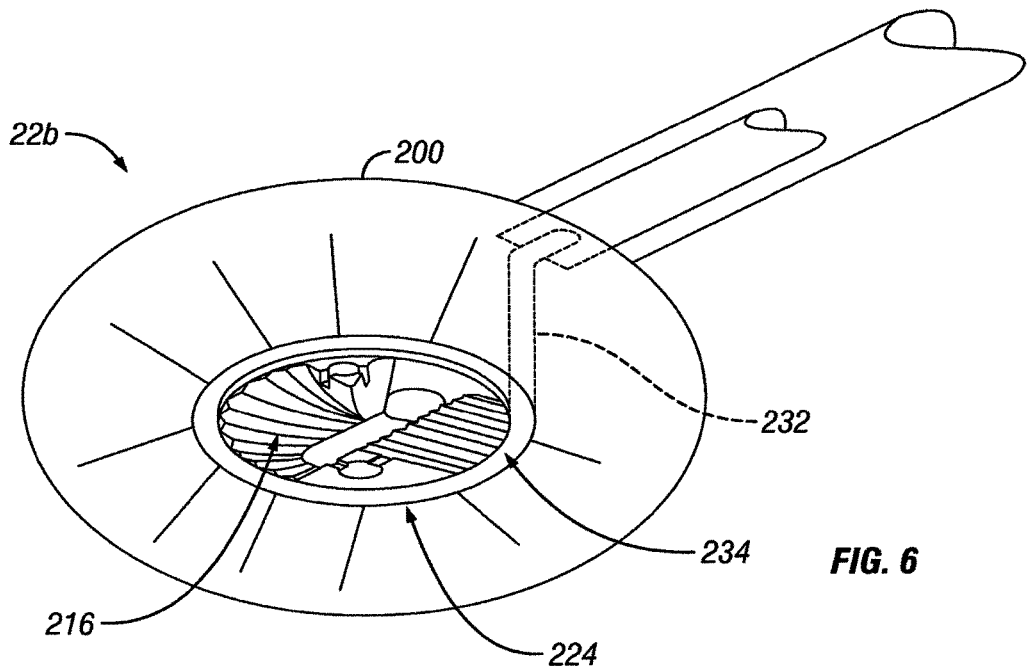
FIG. 6 depicts a bottom perspective view of an alternate embodiment of the connection in FIG. 3.

Referring now to FIG. 6, an alternative embodiment 22b is shown that is substantially similar to connection pad 22a, with the primary exception that connection pad 22b (e.g., in addition to port 136 and open channel 140) comprises a fluid-delivery lumen 232 and fluid-delivery ring 234 disposed around cavity 216 (e.g., around the perimeter of base portion 224 and/or cavity 216), where fluid-delivery lumen 232 is in communication with fluid-delivery ring 234. In this embodiment, fluid delivery ring 234 is configured to permit fluid to be delivered around cavity 216 (e.g., such that a fluid can be delivered from fluid source 50 via fluid lumen 232) and will disperse through at least a portion of (e.g., up to all of) fluid delivery ring 234 such that the fluid will be dispersed around wound insert 24.

Figure 7A:
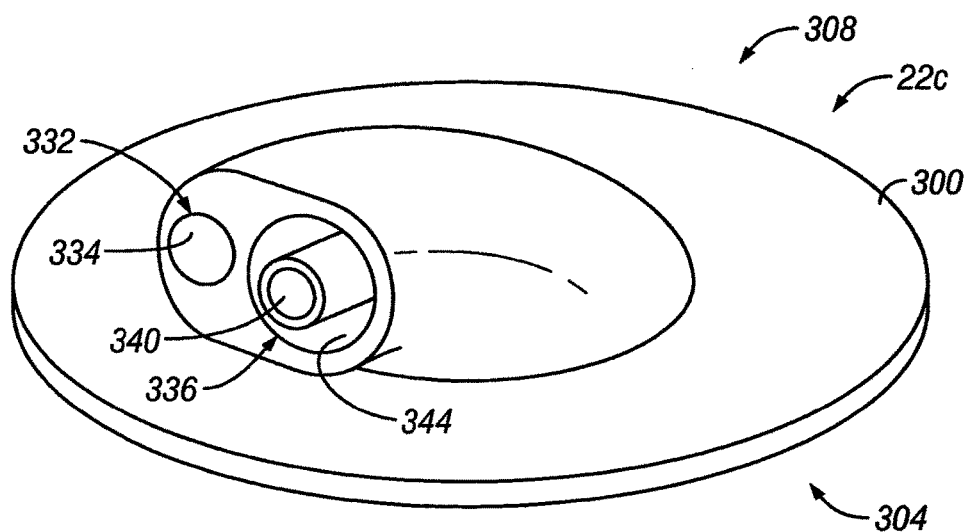
FIG. 7A depicts an upper perspective view of one embodiment of the present connection pads.
Figure 7B:
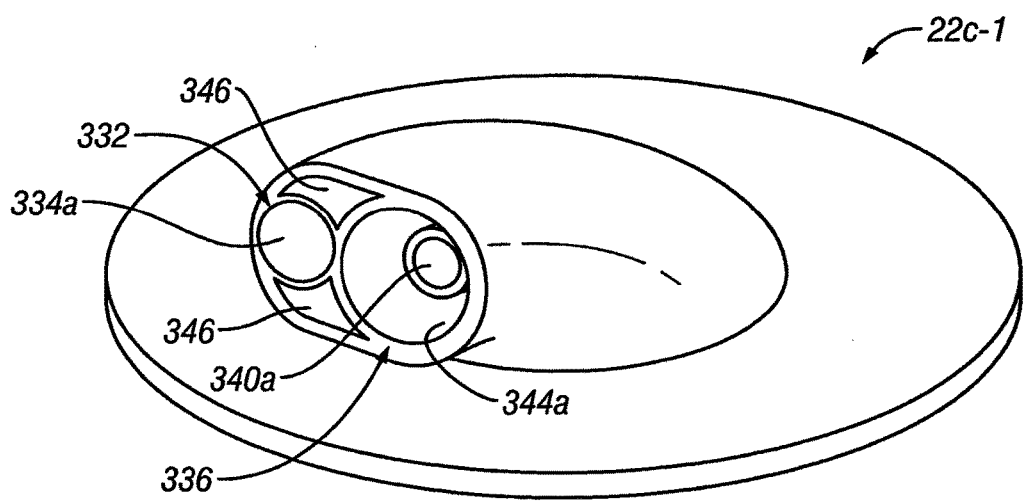
FIG. 7B depicts an upper perspective view of an alternate configuration for the connection pad of FIG. 7A.
Figure 8A:
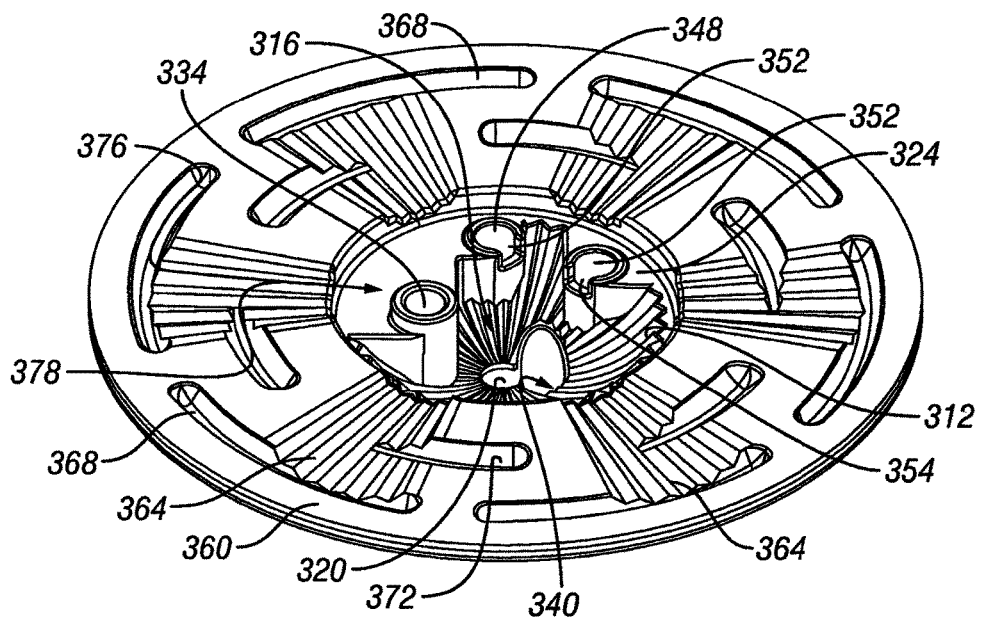
FIG. 8A depicts a lower perspective view of the connection pad of FIG. 7A.
Figure 8B:
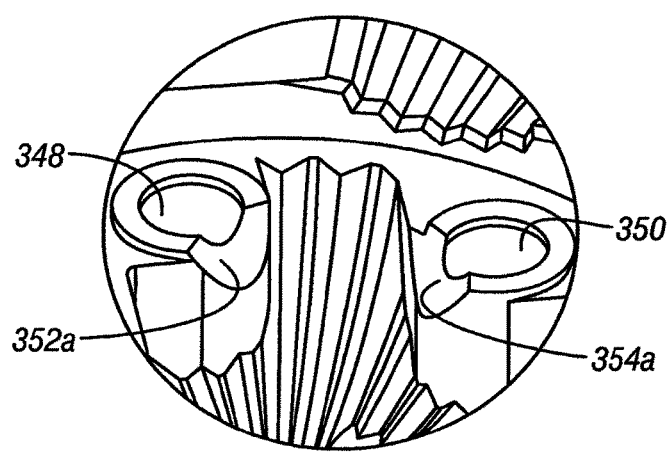
FIG. 8B depicts a lower perspective view of an alternative configuration for the connection pad of FIG. 8A.

Referring now to FIGS. 7A-8B, shown there is another embodiment of a connection pad 22c. FIGS. 7A and 8A depict upper and lower perspective views of connection pad 22c. As described in more detail below, FIGS. 7B and 8B depict alternate configurations for various features of connection pad 22c. Connection pad 22c is similar in some respects to connection pads 22a and 22b, as described in more detail here. In the embodiment shown, connection pad 22c comprises a body 300 and a dressing side 304 and a connection side 308. Dressing side 304 includes a surface 312 defining a cavity 316 (e.g., a domed cavity) having an upper portion 320 and a base portion 324. In the embodiment shown, body 300 also includes a flange 328 (e.g., a substantially planar flange) surrounding base portion 324 of cavity 316. In the embodiment shown, connection side 308 includes a single-lumen fluid delivery connection 332 configured to be coupled to a fluid source (e.g., fluid source 50), and having a lumen 334 extending into cavity 316. In the embodiment shown, connection side 308 also includes a multi-lumen vacuum and pressure-sensor connection 336 configured to be coupled in vacuum apparatus 16). Connection 336 has a vacuum lumen 340 terminating at upper portion 320 of cavity 316, and an annular pressure-sensor lumen 344 disposed around vacuum lumen 340. In a manner similar to that described above for lumens 156, 160 and lumen 132 for connection pad 22a, annular pressure-sensor lumen 344 is not in fluid communication with vacuum lumen 340 through body 300.

FIG. 7B depicts an alternate configuration 22c-1 for connection pad 22c. In particular, connection 332 includes a larger lumen 334a (and/or body 300 is configured such that the sidewall that defines lumen 334a is thinner than in connection pad 22c); connection 336 includes a larger lumen 344a (and/or body 300 is formed such that the sidewall that defines lumen 344a is smaller than in connection pad 22c); connection 336 is configured such that lumen 340a terminates within lumen 344a (e.g., such that the end of lumen 340a terminates inside of, or short of, the end of lumen 344a, as shown); and body 300a includes a plurality of cutouts 346 between lumen 334a and lumen 344a (e.g., to improve ease of manufacture, such as by injection or other molding or casting).

In the embodiment shown, body 300 defines two pressure-sensor lumens 348, 350 each having a lower end, as shown, extending into cavity 316, and each in fluid communication with annular pressure-sensor lumen 344. Additionally, in the embodiment shown, a lateral portion of each pressure-sensor lumen 348, 350 is open to cavity 316. More particularly, in the embodiment shown, body 300 defines notches 352, 354, extending between lateral portions of lumens 348 and 350, respectively. In the embodiment shown, notches 352, 354 are substantially rectangular. In other configurations, notches 352, 354 can have any suitable shape (e.g., angled, arcuate notches 352a, 354a, as shown in FIG. 8B). As described above for notches 180, 182, 184, and 186 of connection pad 22a, notches 352, 354 are configured to improve communication between lumens 348, 350 and cavity 316, so as to improve the ability of vacuum apparatus 16 to sense and/or monitor pressure or negative pressure at the wound (e.g., in cavity 316 and/or in wound dressing 12), especially, for example, where opening 48 in drape 26 is small, roughly cut, not fully made, off center, and/or is otherwise not optimally formed such that drape 26 might otherwise (in the absence of notches 352, 354) interfere and/or partially block the lumens 348 and 350. In other embodiments, body 300 may define more than two pressure centered lumens, and/or notches 352, 354 may be provided with any suitable shape (e.g., such as square or rectangular notches 180, 182 of connection pad 22a). In other embodiments, body 300 may define circumferential castellations around the bottom end of lumens 348 and 350.

In the embodiment shown, connection pad 22c is configured as a vacuum and fluid delivery connection pad with relatively simple connections to a fluid source and a vacuum apparatus, such that fluid may be delivered, negative pressure may be applied, and/or pressure or negative pressure may be sensed by way of the same connection pad 22c. In the embodiment shown, the lower end of fluid-delivery lumen 334 is configured to have a substantially square end (e.g., does not have a lateral portion open to cavity 316). In this way, the lower end of fluid-delivery lumen 334 is configured to substantially abut wound insert 24 if connection pad 22c is coupled to wound insert 12, such that if fluid is delivered through fluid-delivery lumen 334, such fluid is delivered primarily directly into wound insert 24 rather than into cavity 316. In this way, fluid delivered by way of fluid-delivery lumen 334 is dispersed into wound insert 24 such that the fluid or at least some portion of the fluid will reach the wound (e.g., a surface of the wound) to irrigate or deliver medication to the wound, and will be subsequently drawn back through wound insert 24 and guided through cavity 316 to vacuum lumen 344.

Similarly to connection pad 22a, body 300 (e.g., surface 312) of connection pad 22c defines a plurality of grooves 356 extending radially outward from the apex of cavity 316 to base portion 324 of cavity 316. In this embodiment, grooves 356 are configured to guide fluid entering cavity 316 past fluid-delivery lumen 334 and pressure-sensor lumens 348 and 350 to vacuum lumen 344. In this way, grooves 356 assist in preventing and/or reducing fluid and/or exudates from interfering with or blocking pressure-sensor lumens 348, 350 and/or fluid-delivery lumen 334. Body 300 does not include a shelf (such as shelf 172 of connection pad 22a); however, in other embodiments, body 300 may include a shelf.

In the embodiment shown, a lower side 360 of flange portion 328 includes a plurality of features configured to guide fluids from radially outer portions of flange 320 into cavity 316 (e.g., such as when vacuum is applied through vacuum lumen 344). For example, in the embodiment shown lower side 360 includes a plurality of radial grooves, and two circular paths of arcuate grooves, each path including a plurality of arcuate grooves concentric with the cavity (e.g., a plurality of distinct arcuate grooves each lying on one of two circular paths disposed concentrically around the cavity). More particularly, in the embodiment shown, lower side 360 of flange 328 includes a plurality of radial serrated guide channels 364, a plurality of arcuate perimeter collection channels 368, and a plurality of arcuate intermediate collection channels 372. In the embodiment shown, each serrated guide channel 364 extends radially outward from cavity 316 to a corresponding arcuate perimeter collection channels 368 at a point internal to the outer perimeter of flange portion 328. In the embodiment shown, each serrated guide channel 364 is deepest at its center and is shallower at its lateral edges. More particularly, each serrated guide channel 364 comprises a central groove or serration having a depth, and a plurality of peripheral grooves or serrations adjacent the central groove or serration, and each peripheral groove or serration has a depth that is less than the depth of the central groove (e.g., having depths that are sequentially less as the distance between the peripheral groove and the central groove increases).

In the embodiment shown, each arcuate perimeter collection channel 368 extends from a distal (relative to cavity 316) end of a corresponding serrated guide channel 364 in a clockwise direction from the corresponding serrated guide channel 368, and terminates before reaching the next adjacent serrated guide channel 364, as shown. In the embodiment shown, arcuate perimeter collection channels 368 are concentric with cavity 316. Each arcuate intermediate collection channel 372 extends from the center of a corresponding serrated guide channel 368 in a counterclockwise direction from the corresponding serrated guide channel 368, and terminates before reaching the next adjacent serrated guide channel 368, as shown. In the embodiment shown, arcuate intermediate collection channels 372 are concentric with cavity 316, and concentric with arcuate perimeter collection channels 368. Serrated guide channels 364, arcuate intermediate collection channels 372, and arcuate perimeter collection channels 368 are configured to cooperate to guide fluid from the periphery of flange 328 to cavity 316 in the manner indicated by arrows 376 and 378. In other embodiments, arcuate perimeter collection channels 368 and/or arcuate intermediate collection channels 372 can be provided in any suitable number and/or direction.

In the embodiment shown, connection pad 22c is configured such that the lower side of flange portion 328 is configured to face wound dressing 12 (e.g., wound insert 24) if connection pad 22c is coupled to wound dressing 12. In some embodiments, connection pad 22c comprises and/or is provided with a ring of adhesive (not shown) such as described above for connection pad 22a (e.g., coupled to an upper side of flange portion 328 and/or coupled to a peripheral portion of the lower side of flange portion 328).

Figure 9:
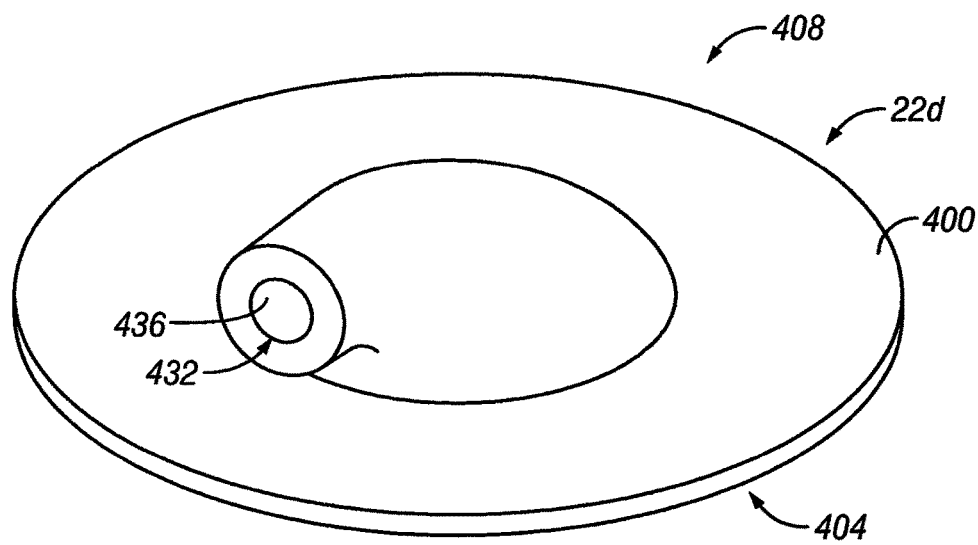
FIG. 9 depicts a perspective view of another embodiment of the present connection pads.
Figure 10:
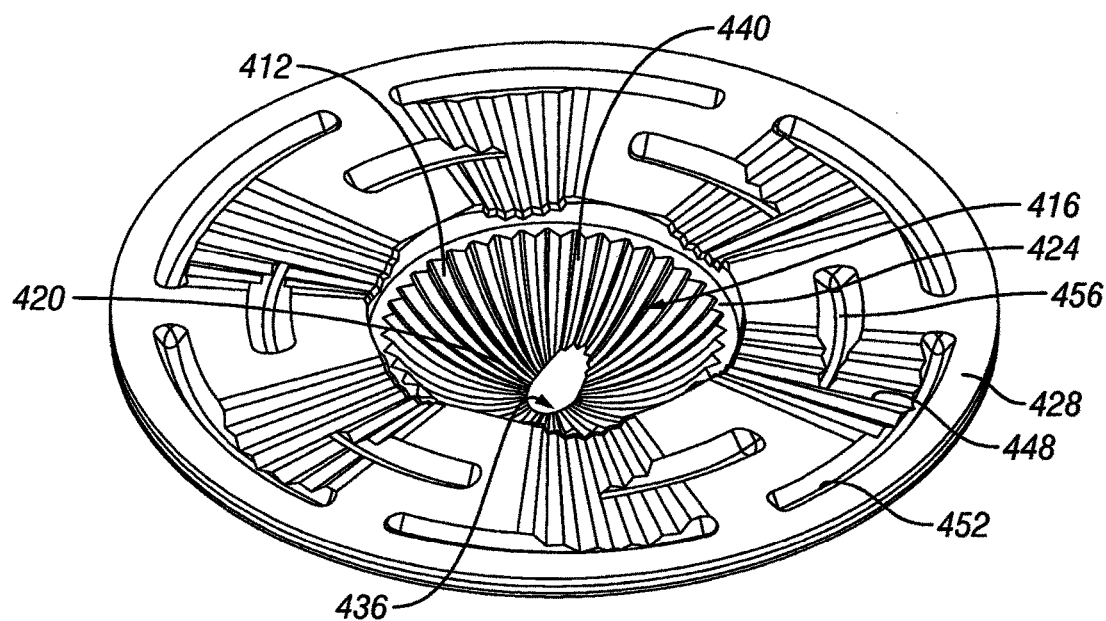
FIG. 10 depicts a lower perspective view of the connection pad of FIG. 9.

Referring now to FIGS. 9 and 10, another embodiment 22d is shown of one of the present connection pads. Connection pad 22d is similar in some respect to connection pads 22a, 22b, and 22c, as described here. In the embodiment shown, connection pad 22d comprises a body 400 having a dressing side 404 and a connection side 408. Dressing side 404 includes a surface 412 defining a cavity 416 (e.g., a domed cavity) having an upper portion 420 and a base portion 424. In the embodiment shown, body 400 also includes a flange 428 (e.g., a substantially planar flange) surrounding base portion 424 of cavity 416. Connection side 408 includes a fluid delivery connection 432 having a fluid-delivery lumen 436 in fluid communication with upper portion 420 of cavity 416, and configured to be coupled to a fluid source (e.g., fluid source 50). Additionally, in the embodiment shown, surface 412 defining cavity 416 includes a plurality of grooves 440 extending from upper portion 420 of cavity 416 to base portion 424 of cavity 416.

In the embodiment shown, cavity 416 does not include a shelf (e.g., shelf 172 of connection pad 22a), such that the entirety of cavity 416 is domed in an arcuate circular configuration (e.g., a hemispherical configuration). As such, in the embodiment shown, fluid-delivery lumen 436 extends to upper portion 420 of cavity 416, and grooves 440 extend radially outward along surface 412 from fluid-delivery lumen 436 to base portion 424 of cavity 416. In the embodiment shown, a lower surface 444 of flange 428 includes serrated guide channels 448, arcuate perimeter collection channels 452, arcuate intermediate collection channels 456, which are substantially similar to serrated guide channels 364, arcuate perimeter collection channels 368, and arcuate intermediate collection channels 372 of connection pad 22c, described above.

In the embodiment shown, connection pad 22d is configured for fluid delivery such that connection pad 22d can be coupled to a fluid source (e.g. fluid source 50) and to wound dressing 12, such that a separate connection pad can also be separately coupled to wound dressing 12 and to a vacuum source (e.g., vacuum apparatus 16), to separately apply vacuum to wound dressing 12. In this way, distance between fluid delivery connection pad 22d in a vacuum connection can be maximized such that fluid delivered through connection pad 22d is more likely to travel through wound insert 24 and to the wound surface before being extracted through the vacuum connection pad. As such, connection pad 22d may also be characterized or described as a fluid instillation connection pad 22d.

Figure 11:
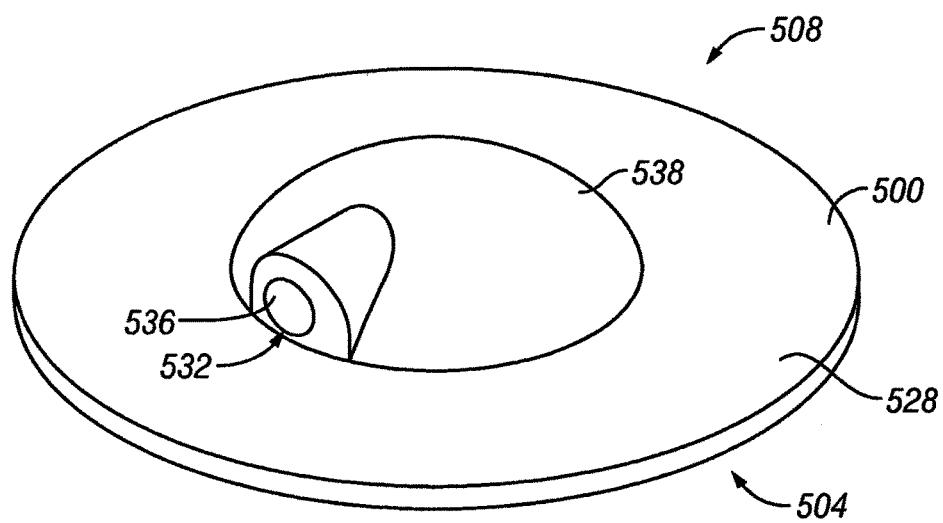
FIG. 11 depicts an upper perspective view of another embodiment of the present connection pads.
Figure 12A:
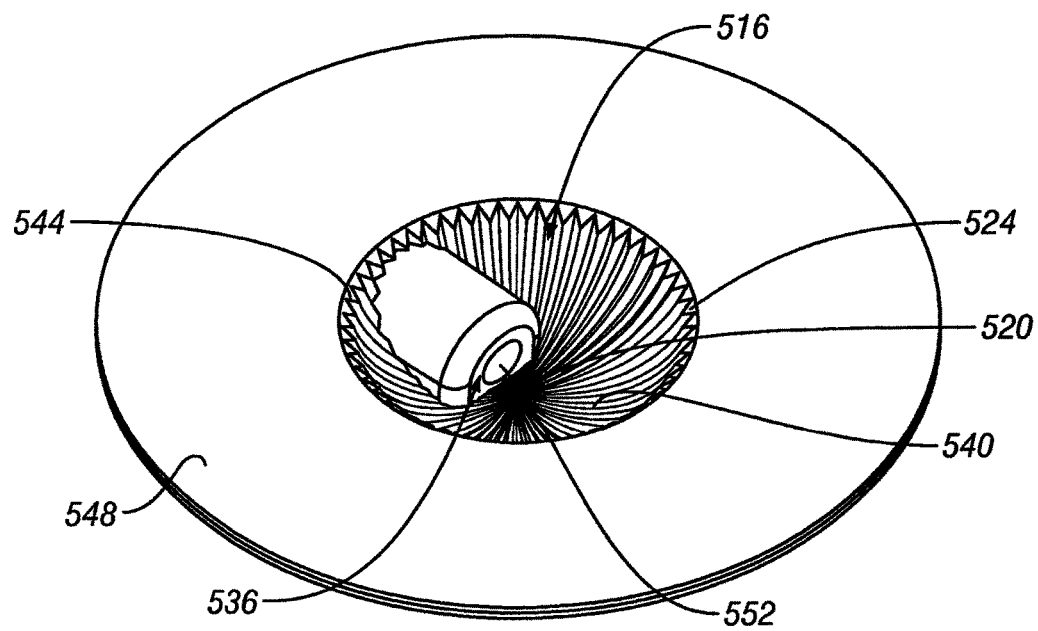
FIG. 12A depicts a lower perspective view of the connection pad of FIG. 11.

Referring now to FIGS. 11 and 12A, another embodiment 22e of the present connection pads is shown. Connection pad 22e is similar in some respect to connection pads 22a, 22b, 22c, and 22d, as described here. In the embodiment shown, connection pad 22e comprises a body 500 having a dressing side 504 and a connection side 508. Dressing side 504 includes a surface 512 defining a cavity 516 (e.g., a domed cavity) having an upper portion 520 and a base portion 524. In the embodiment shown, body 500 also includes a flange 528 (e.g., a substantially planar flange) surrounding base portion 524 of cavity 516. Connection side 508 includes a fluid delivery connection 532 having a fluid-delivery lumen 536 in fluid communication with upper portion 520 of cavity 516, and configured to be coupled to a fluid source (e.g., fluid source 50). In the embodiment shown, body 500 is configured such that delivery connection 532 does not extend beyond the perimeter of dome 538. In this way, a drape (e.g., 26) can be configured to have an opening (e.g., 48) having a diameter that is substantially equal to were slightly larger than the perimeter of dome 538 such that wound insert 24 can be placed on or in a wound of a patient, connection pad 22e can be placed in contact with wound insert 24, and a drape with an appropriately sized hole can be placed over connection pad 22e (e.g., body 500) such that dome 538 extends through the opening in the drape in the drape can be adhered to flange portion 528 with relative ease and/or relatively little wrinkling or modification. In certain the embodiments, any of other connection pads 22a, 22b, 22c, 22d can be configured in similar fashion such that the various connections on their respective connection side did not extend beyond the perimeter of the domed portions on their respective upper sides (e.g., corresponding to their respective domed cavities).

Figure 12B:
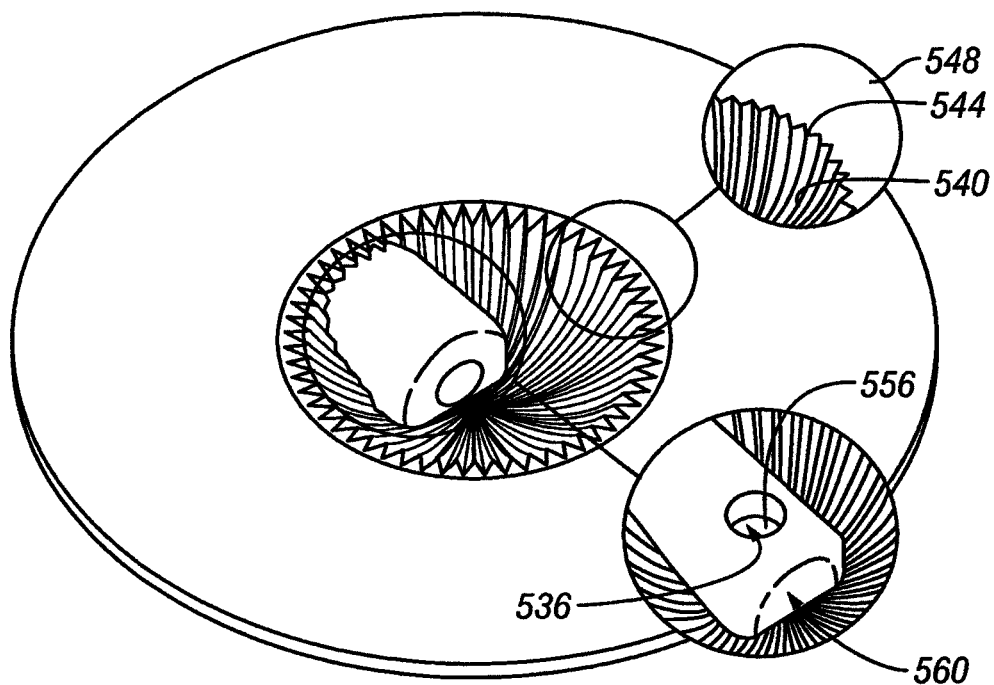
FIG. 12B depicts alternate configurations for certain features of the connection pad of FIGS. 11 and 12A.

In the embodiment shown, surface 512 defining cavity 516 includes a plurality of grooves 540 extending from upper portion 520 of cavity 516 to base portion 524 of cavity 516. Additionally, in the embodiment shown, base portion 524 of cavity 516 has a lower peripheral edge 544 with a saw-toothed configuration, as shown. In the embodiment of FIG. 12, the saw-toothed configuration of edge 544 is formed by the intersection of a chamfer between grooves 544 and lower surface 548 of flange 528. In the configuration shown in the upper inset of FIG. 12B, the chamfer is omitted such that the saw-toothed configuration is provided by the intersection of grooves 540 and lower surface 548 of flange 528. In the embodiment shown, lower surface 548 is substantially smooth and substantially planar, as shown. In this way, and as particularly suited for fluid delivery connection pads, substantially smooth planar lower surface 548 can be coated with and/or coupled to an adhesive such that substantially all of lower surface 548 can be coupled to wound insert 12 (e.g. to wound insert 24) to provide adhesion between lower surface 548 and wound dressing 12 (e.g., wound insert 24 and/or drape 26) to provide a connection that is durable in the presence of liquid (e.g., resistance to degradation in the presence of liquids such as water or the like). As also shown, fluid-delivery lumen 536 extends laterally into cavity 516 between upper portion 520 and base portion 524. Additionally, in the embodiment shown, fluid-delivery lumen 536 includes an open-end 552 facing (e.g., directed toward) a side of cavity 516.

In other embodiments, such as is shown in the lower inset of FIG. 12B, a lateral portion of fluid-delivery lumen 536 opens downward toward base portion 524 of cavity 516. More particularly, and the embodiment shown, body 500 defines an aperture 556 opening downward into cavity 516 toward base portion 524. Additionally, in the embodiment shown in the lower inset of FIG. 12B, the end 560 of fluid-delivery lumen 536 is closed such that fluid-delivery lumen 536 is only in fluid communication with cavity 516 through downward opening or aperture 556 from fluid-delivery lumen 536. Similarly to connection pads 22a, 22b, 22c, and 22d; connection pad 22e can be provided with a ring of adhesive (not shown) either or both of an upper or lower side of flange 528, such that flange 528 can be configured to be coupled to wound dressing 12 (e.g., to wound insert 24). The embodiment shown, flange portion 528 of body 500 is configured such that lower surface or side 548 faces wound dressing 12 (e.g., wound insert 24) such as where an adhesive is coupled to lower surface 548 of flange 528.

Figure 12C:
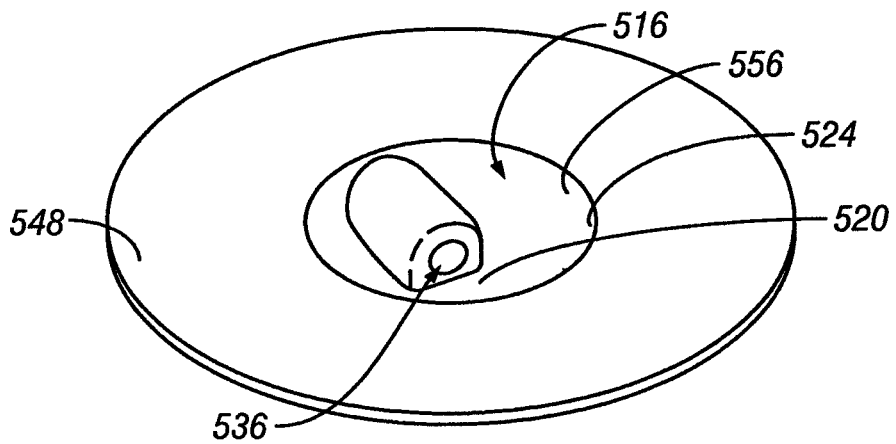
FIG. 12C depicts a lower perspective view of an alternate embodiment of the connection pad of FIG. 11.

FIG. 12C depicts another embodiment that is substantially similar to the embodiment of FIG. 12A, but in which cavity 516 does not include grooves, and instead includes a substantially smooth interior surface 556.

Figure 13:
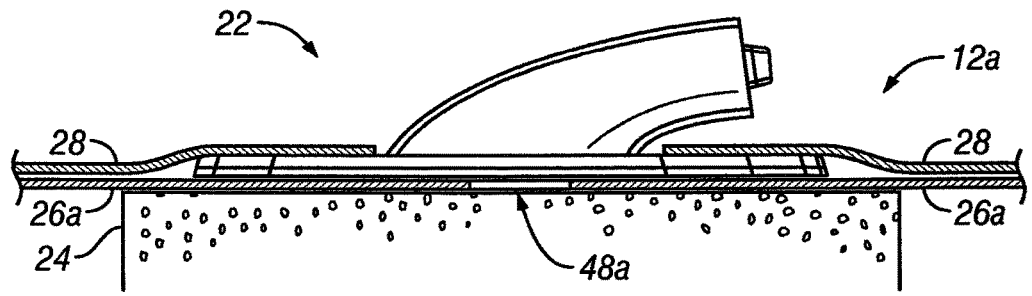
FIG. 13 depicts a partially cross-sectional view of one of the present connection pads coupled to an embodiment of the present wound dressings.

Referring now to FIG. 13, one of the present connection pads 22 is shown coupled to a wound dressing 12a. For clarity, wound dressing 12a is shown in cross-section. More particularly, in the embodiment shown, wound dressing 12a comprises: a wound insert 24 (e.g., adjacent a wound or wound surface of a patient); a drape 26a (e.g., coupled to skin adjacent the wound) such that drape 26a covers the wound and wound insert 24 and forms a space between the wound and drape 26a. Additionally in the configuration shown, wound dressing 12a further comprises a secondary drape 28 coupling connection pad 22 to drape 26. In the embodiment shown, drape 26a is substantially similar to drape 26 of FIG. 2, but includes a user-made hole 48a. That is, when a user such as a nurse or doctor opens drape 26a for use (e.g., from a package), the user must cut drape 26a to form hole 48a. In such embodiments hole 48a may be smaller than desired, smaller than optimally effective, and/or may be jagged or irregular such that flaps of drape 26a may interfere with pressure-sensor lumens of previously known connection pads. As such, embodiments of the present connection pads (e.g. 22a, 22c) are configured for improved functionality where such connection pads are coupled to wound dressings in a configuration such as is shown in FIG. 13. For example, and as noted above, body 100 of connection pad 22a has lateral portions of the pressure-sensor lumens 156 and 160 (e.g., by way of notches 180, 182, 184, 186) open into or in communication with cavity 116 to enable improved pressure-sensor functionality where connection pad 22a is coupled to a wound dressing in a configuration such as is shown in FIG. 13 (e.g., between a first drape and a second drape such that the connection pad is not in direct contact with the wound insert).

Some embodiments of the present wound-treatment methods comprise: coupling a wound dressing (e.g., wound dressing 12) to a patient; coupling one or more of any of the present connection pads to the wound addressing; delivering a fluid to the wound dressing (e.g. to a wound covered by the wound dressing); applying a vacuum to the wound dressing (e.g., to a wound covered by the wound dressing); and/or sensing a pressure or negative pressure in the wound dressing (e.g., at a wound covered by the wound dressing), such as, for example, while delivering a fluid to the wound dressing and/or while applying a vacuum to the wound dressing; backspace. In any of the embodiments of the present wound-treatment methods, coupling a wound dressing to a patient can comprise: disposing a wound insert adjacent to a wound of a patient (e.g., on a wound surface of the wound); and/or coupling a drape to skin of the patient adjacent to the wound such that the drape covers the wound insert in the wound and forms a space between the wound and the drape. In any of the embodiments of the present wound-treatment methods, coupling one or more of any of the present connection pads to the wound dressing can comprise coupling the connection pad to the wound insert (e.g., before or after coupling the drape to the skin of the patient); and/or coupling the drape to the connection pad (e.g., before or after coupling the drape to the skin of the patient). In any embodiments of the present wound-treatment methods, delivering a fluid to the wound dressing can comprise activating a fluid source (e.g., fluid source 50) to deliver a fluid to the wound dressing. In any of the embodiments of the present wound-treatment methods, applying a vacuum to the wound dressing can comprise activating a vacuum source (e.g. vacuum apparatus 16) to apply a vacuum or negative pressure to the wound dressing in any of the embodiments of the present wound-treatment methods, possessing a pressure or negative pressure in the wound dressing can comprise activating one or more pressure censors or pressure-sensor elements (e.g., pressure-sensor elements 40a, 40b) to sense a pressure or negative pressure in wound dressing 12 (e.g., in the space formed between the wound in the drape).

Figure 14:
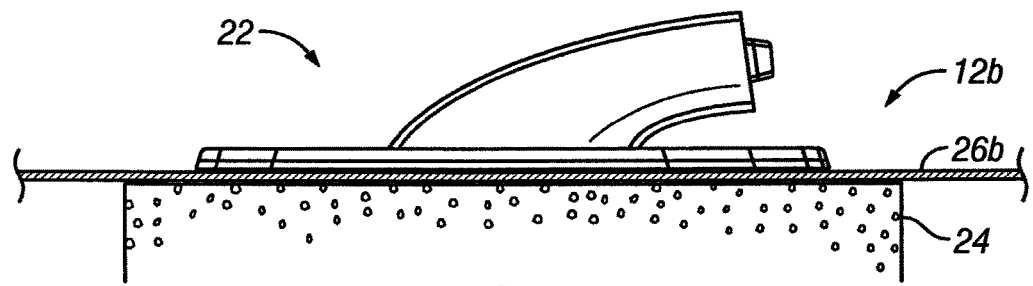
FIG. 14 depicts a partially cross-sectional view of one of the present connection pads coupled to another embodiment of the present wound dressings, before a drape of the wound dressing is breached.
Figure 15:
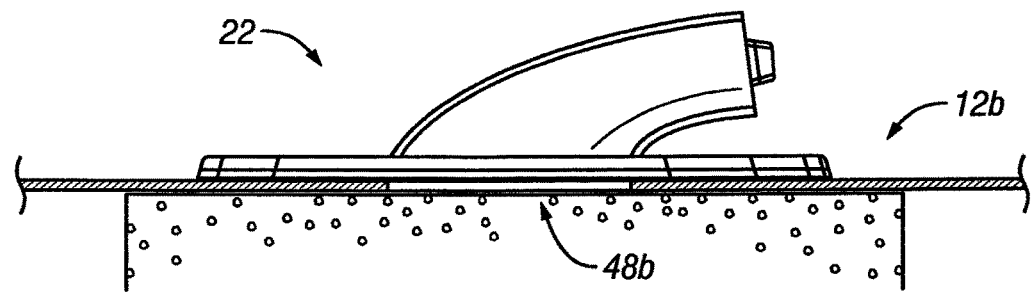
FIG. 15 depicts a partially cross-sectional view of the connection pad coupled to the present wound dressing of FIG. 14, after the drape of the wound dressing has been breached.

Referring now to FIGS. 14 and 15, an additional embodiment of a wound dressing 12b is shown. In the embodiment shown, wound dressing 12b comprises a drape 26b and the wound insert 24. More particularly, in the embodiment shown, wound insert 12b is shown in a coupled configuration such that wound insert 24 is adjacent a wound of a patient (e.g., is adjacent a wound surface of the wound) and drape 26b is coupled to skin (not shown) adjacent the wound. As shown, drape 26b has not been breached (e.g., does not have a hole such as hole 48 of drape 26). In this way, wound insert 24 can be placed adjacent the wound, and drape 26b can be coupled to skin adjacent a wound to cover the wound and the wound insert 24 such that the wound insert and the wound are substantially sealed by drape 26b, as shown in FIG. 14. In the embodiment shown, connection pad 22 is coupled to drape 26b by way of adhesive between a lower side of the flange portion of connection pad 22 and drape 26b, and after connection pad 22 is coupled to drape 26b and drape 26b is breached to create a hole 48b, as shown in FIG. 15. In some embodiments, wound insert 12b can comprise a secondary drape 28 (e.g., similar to secondary drape 28 of FIG. 13) to couple connection pad 22 to wound dressing 12b.

In accordance with the configuration depicted in FIGS. 14 and 15, embodiments of the present methods of coupling a wound dressing to a patient comprise: disposing a wound insert (e.g., wound insert 24) adjacent to a wound of a patient (e.g., adjacent to and/or in contact with a surface of the wound); coupling a drape (e.g., drape 26b) to skin of the patient adjacent the wound such that the drape covers the wound insert and the wound and defines a space (e.g., space that is at least partially and/or entirely open); coupling a connection pad (e.g., connection pad 22, 22a, 22b, 22c, 22d, 22e) to the drape, where the fluid delivery pad is configured to be coupled to a fluid source (e.g., fluid source 50) such that the fluid source can deliver fluid to the connection pad. In some embodiments the drape is configured to comprise a substantially solid sheet (e.g., a sheet without a hole such as hole 48). In some embodiments of the present methods of coupling a wound dressing to a patient comprise breaching the drape, after coupling section pad to the drape fluid communication between the wound dressing (e.g., the space between the wound surface and the drape).

In some embodiments, breaching the drape comprises delivering (e.g., from a fluid source, such as a fluid pump or syringe, through a conduit coupled to the connection pad) through the connection pad a solvent to the drape, where the solvent is configured to dissolve a portion of the drape (e.g., dissolves a portion of the drape sufficient to create a hole 48b) to permit fluid communication between the space and the connection pad (e.g. between a fluid source coupled to the connection pad and the space between the drape and the wound surface. For example, currently available drapes often comprise polyurethane, which is generally dissolvable in or with solvents that comprise ketones. As such, suitable solvents may comprise ketones (e.g., propanone) and/or other solvents or components that are soluble in water (or other embodiments, insoluble in water). In such embodiments, to prevent the solvent from dissolving the fluid delivery conduit (e.g., 54) end of the connection pad, they conduit and the connection pad can comprise a material that is not soluble in the presence of the solvent used. For example, in the embodiments in which the solvent comprises a ketone, the fluid delivery conduit and the connection pad can comprise suitably insoluble polymers (e.g. and soluble in the presence of the solvent used), such as, for example, thermoplastic elastomers. By way of another example, the fluid delivery conduit may have a liner co-extruded or co-molded into the interior of the conduit, such that the liner is insoluble in the presence of the solvent used and thereby protects the conduit. Similarly, wound insert 24 should comprise a material that is at least substantially insoluble in the presence of the solvent, such that introduction of the solvent to the drape and breaching of the drape by the solvent does not substantially degrade the foam of wound insert 24.

Alternatively, the drape can comprise a polymer or other material soluble in a less-aggressive solvent, such that commonly available connection pads and conduits may be used. For example drape can comprise a vinyl acetate copolymer configured to be soluble in various alcohols, such as, for example, ethanol and the like. By way of another example, the drape can comprise a polymer with free acid groups attached (e.g., acrylics and the like) configured to be soluble in water with high pH levels, such that, for example, the solvent can comprise water comprising salts (e.g., carbonates), amines (e.g., urea, or ethanolamine), and or the like such that the water is configured to have a high pH level (e.g., equal to, greater than, less than, or between any of, 7, 8, 9, 10, 11, 12, 13, 14).

In the embodiment shown in FIGS. 14 and 15, connection pad 22 comprises a dressing side with the cavity, as is described above for the various embodiments of the present connection pads. Some embodiments of the present methods comprise disposing a container (e.g., such as a balloon, envelope, or the like) of a first solvent between the connection pad and the drape (e.g. within a cavity of the connection pad), where the first solvent is configured to dissolve a portion of the drape, and where the container is configured to dissolve in the presence of a second solvent. In such embodiments of the present methods, breaching the drape can comprise delivering the second solvent to the container (e.g. through the connection pad and/or from a fluid source such as fluid source 50) such that the container dissolves to release the first solvent and the first solvent dissolves a portion of the drape (e.g., dissolves a portion of the drape sufficient to create a hole 48b).

Some embodiments of the present methods further comprise: delivering a fluid to the wound dressing through the connection pad, and/or applying a vacuum to the wound dressing (e.g., after delivering a fluid to the wound dressing, such as through the connection pad through which fluid is delivered and/or another connection pad), to flush away debris from hole 48b (e.g., dissolve drape material) and/or to flush away remaining solvent such that dissolution of the drape is halted or stopped after a predetermined amount of time or after hole 48*b* reaches a desired or predetermined sized. For example, such a fluid can comprise an inert fluid, such as, for example, water, saline solution, and/or the like.

Embodiments of the present methods in which the drape is breached after a connection pad is coupled to the drape are configured to prevent and/or produce user error and difficulty associated with requiring a user to create a hole in the drape. For example, breaching the drape in the ways described in the present methods automatically creates the hole in the drape and position corresponding with the appropriate lumens of the connection pad (e.g. corresponding to a cavity of the connection pad), and thereby can improve performance, reliability, and repeatedly of the various wound-treatment methods including the present wound dressings and connection pads.

Embodiments of the present drapes, connection pads, and the like are configured to have the features described in this disclosure (e.g., for the present methods).

The various illustrative embodiments of devices, systems, and methods described herein are not intended to be limited to the particular forms disclosed. Rather, they include all modifications and alternatives falling within the scope of the claims.

The claims are not intended to include, and should not be interpreted to include, means-plus- or step-plus-function limitations, unless such a limitation is explicitly recited in a given claim using the phrase(s) "means for" or "step for," respectively. It will be understood that the benefits and advantages described above may relate to one embodiment or may relate to several embodiments. It will further be understood that reference to 'an' item refers to one or more of those items, unless otherwise specified.

The steps of the methods described herein may be carried out in any suitable order, or simultaneously where appropriate.

Where appropriate, aspects of any of the examples described above may be combined with aspects of any of the other examples described to form further examples having comparable or different properties and addressing the same or different problems.

It will be understood that the above description of preferred embodiments is given by way of example only and that various modifications may be made by those skilled in the art. The above specification, examples and data provide a complete description of the structure and use of exemplary embodiments. Although various embodiments have been described above with a certain degree of particularity, or with reference to one or more individual embodiments, those skilled in the art could make numerous alterations to the disclosed embodiments without departing from the scope of this invention.

The invention claimed is:

1. Connection pads for providing vacuum and fluid to a wound insert adapted to be in fluid communication with a wound, comprising:
   a fluid-delivery connection pad comprising a first body including a first domed cover having a dressing side and a connection side, the dressing side forming a first cavity having an upper portion and a base portion adapted to be disposed proximate a wound insert, and a first flange extending radially outward from the first domed cover and defining a terminus of the base portion, the first domed cover having a fluid lumen connection on the connection side configured to be coupled to a fluid source and having a fluid-delivery lumen on the dressing side extending from the fluid lumen connection and terminating proximate to the terminus for providing fluid to the wound insert; and
   a vacuum connection pad comprising a second body including a second domed cover having a dressing side and a connection side, the dressing side forming a second cavity having an upper portion and a base portion adapted to be disposed proximate a wound insert, and a second flange extending radially outward from the second domed cover and defining a terminus of the base portion, the second domed cover having a multi-lumen connection on the connection side configured to be coupled to a vacuum source and a pressure sensor, and having (a) a vacuum lumen on the dressing side terminating within the upper portion for providing a vacuum to the wound insert, and (b) a first pressure-sensor lumen on the dressing side extending from the multi-lumen connection and having an open end terminating proximate to the terminus, the open end including a lateral portion adjacent the open end having an opening extending into the base portion of the second cavity.

2. The connection pads of claim 1, wherein the second domed cover includes a second pressure-sensor lumen on the dressing side extending from the multi-lumen connection and having an open end terminating proximate to the terminus, the open end including a lateral portion adjacent the open end having an opening extending into the base portion of the second cavity.

3. The connection pads of claim 2, wherein the multi-lumen connection comprises an annular pressure-sensor lumen disposed around the vacuum lumen, the annular pressure-sensor lumen in communication with the first and/or second pressure-sensor lumen(s).

4. The connection pads of claim 1, further comprising a fluid-delivery ring fluidly coupled to the fluid-delivery lumen and disposed around at least a portion of the first cavity and configured to permit fluid to be delivered around the first cavity in fluid communication with the wound insert.

5. The connection pads of claim 1, wherein at least a portion of the dressing side of the second domed cover includes a plurality of grooves extending from the upper portion to the base portion of the second cavity.

6. The connection pads of claim 1, wherein the second flange comprises a lower edge having a plurality of radial guide channels extending radially outward from the base portion of the second cavity and terminating within the second flange.

7. The connection pads of claim 6, wherein the radial guide channels are each serrated perpendicular to a radial direction.

8. The connection pads of claim 6, wherein the lower edge of the second flange comprises a plurality of arcuate collection channels concentric with the second cavity, each arcuate collection channel extending around a portion of the second cavity.

9. The connection pads of claim 8, wherein the arcuate collection channels include a plurality of arcuate perimeter collection channels and a plurality of arcuate intermediate collection channels that are disposed between the arcuate perimeter collection channels and the second cavity.

10. The connection pads of claim 9, wherein the plurality of radial guide channels extend outward from the base portion of the second cavity and each terminate at one of the arcuate perimeter collection channels.

11. The connection pads of claim 6, wherein each of the radial guide channels is serrated perpendicular to a radial direction and comprises serrations with different depths.

12. The connection pads of claim 11, wherein each radial guide channel comprises a central serration having a depth and a plurality of peripheral serrations adjacent the central serration, each peripheral serration having a depth that is less than the depth of the central serration.

13. The connection pads of claim 1, wherein at least a portion of the dressing side of the second domed cover further defines a shelf parallel to and/or coplanar with the second flange adjacent the base portion of the second cavity.

14. The connection pads of claim 1, wherein the first pressure-sensor lumen is not in fluid communication with the fluid-delivery lumen.

15. The connection pads of claim 1, further comprising a ring of adhesive coupled to at least one of the first flange and the second flange.

16. The connection pads of claim 15, wherein the adhesive comprises a hydrogel.

17. The connection pads of claim 15, wherein the adhesive comprises a pressure-sensitive adhesive.

18. The connection pads of claim 15, wherein the first and second flanges each have a lower surface configured to face a wound dressing if the respective connection pad is coupled to a wound dressing, and wherein the adhesive is coupled to the lower surfaces.

19. The connection pads of claim 1, wherein at least one of the first flange and the second flange is configured to be coupled to a drape by at least one of: radio-frequency (RF) welding, ultrasonic welding, or adhesive.

20. The connection pads of claim 1, wherein at least one of the first flange and the second flange is coupled to a drape of a wound dressing.

21. The connection pads of claim 20, wherein at least one of the first flange and the second flange is coupled to the drape by at least one of: radio-frequency (RF) welding, ultrasonic welding, or adhesive.

22. The connection pads of claim 1, wherein at least a portion of the dressing side of the first domed cover includes a plurality of grooves extending from the upper portion to the base portion of the first cavity.

23. The connection pads of claim 1, wherein the first flange comprises a lower edge having a plurality of radial guide channels extending radially outward from the base portion of the first cavity and terminating within the first flange.

24. The connection pads of claim 23, wherein the radial guide channels are each serrated perpendicular to a radial direction.

25. The connection pads of claim 23, wherein the lower edge of the first flange comprises a plurality of arcuate collection channels concentric with the first cavity, each arcuate collection channel extending around a portion of the first cavity.

26. The connection pads of claim 25, wherein the arcuate collection channels include a plurality of arcuate perimeter collection channels and a plurality of arcuate intermediate collection channels that are disposed between the arcuate perimeter collection channels and the first cavity.

27. The connection pads of claim 26, wherein the plurality of radial guide channels extend outward from the base portion of the first cavity and each terminate at one of the arcuate perimeter collection channels.

28. The connection pads of claim 23, wherein each of the radial guide channels is serrated perpendicular to a radial direction and comprises serrations with different depths.

29. The connection pads of claim 28, wherein each radial guide channel comprises a central serration having a depth and a plurality of peripheral serrations adjacent the central serration, each peripheral serration having a depth that is less than the depth of the central serration.

30. The connection pads of claim 1, wherein the second flange has a lower surface substantially even with the open end of the first pressure-sensor lumen and the terminus of the base portion of the second cavity.

* * * * *